United States Patent
Black et al.

(10) Patent No.: US 11,806,037 B2
(45) Date of Patent: Nov. 7, 2023

(54) DAMPING RINGS FOR AN ULTRASONIC SURGICAL INSTRUMENT

(71) Applicant: Cilag GmbH International, Zug (CH)

(72) Inventors: Brian D. Black, Loveland, OH (US); Matthew T. Stone, Mason, OH (US); Andrew T. Beckman, Cincinnati, OH (US); Charles J. Scheib, Loveland, OH (US)

(73) Assignee: Cilag GmbH International, Zug (CH)

(*) Notice: Subject to any disclaimer, the term of this patent is extended or adjusted under 35 U.S.C. 154(b) by 230 days.

(21) Appl. No.: 17/077,152

(22) Filed: Oct. 22, 2020

(65) Prior Publication Data

US 2022/0125461 A1     Apr. 28, 2022

(51) Int. Cl.
*A61B 17/32* (2006.01)
*A61B 34/30* (2016.01)

(52) U.S. Cl.
CPC ...... *A61B 17/320068* (2013.01); *A61B 34/30* (2016.02); *A61B 2017/320074* (2017.08); *A61B 2017/320088* (2013.01)

(58) Field of Classification Search
CPC ............ A61B 17/32; A61B 17/320068; A61B 17/320092; A61B 34/30; A61B 2017/320088; A61B 2017/320074; A61B 2017/320072
See application file for complete search history.

(56) References Cited

U.S. PATENT DOCUMENTS

| | | | |
|---|---|---|---|
| 7,273,483 B2* | 9/2007 | Wiener | A61B 17/320068 606/169 |
| 7,354,440 B2 | 4/2008 | Truckal et al. | |
| 7,381,209 B2 | 6/2008 | Truckai et al. | |
| 8,142,461 B2 | 3/2012 | Houser et al. | |
| 8,663,220 B2 | 3/2014 | Wiener et al. | |

(Continued)

FOREIGN PATENT DOCUMENTS

| | | |
|---|---|---|
| JP | H03-277359 A | 12/1991 |
| WO | WO 2014/004099 A1 | 1/2014 |

OTHER PUBLICATIONS

European Examination Report dated Mar. 6, 2023 for Application No. EP 21806361.8, 4 pgs.

(Continued)

*Primary Examiner* — Vi X Nguyen
(74) *Attorney, Agent, or Firm* — Frost Brown Todd LLP

(57) ABSTRACT

An ultrasonic surgical instrument includes an end effector having an ultrasonic blade, an ultrasonic transducer assembly, and a shaft assembly the shaft assembly includes a tube, an acoustic waveguide, and a sheath radially positioned between the acoustic waveguide and the tube. The acoustic waveguide is received within the tube and is acoustically connected between the ultrasonic blade and ultrasonic transducer assembly to communicate ultrasonic vibrations from the ultrasonic transducer assembly to the ultrasonic blade. The acoustic waveguide extends along a longitudinal axis. The sheath includes a sheath body having an outer body surface and a plurality of damping rings radially extending from the outer body surface and engaged with the tube. The plurality of damping rings are configured to acoustically isolate the acoustic waveguide from the tube.

15 Claims, 25 Drawing Sheets

(56) References Cited

U.S. PATENT DOCUMENTS

| | | | |
|---|---|---|---|
| 8,986,302 B2 | 3/2015 | Aldridge et al. | |
| 9,763,690 B2 | 9/2017 | Rupp et al. | |
| 9,949,785 B2 | 4/2018 | Price et al. | |
| 10,893,884 B2 | 1/2021 | Stoddard et al. | |
| 11,224,491 B2 | 1/2022 | Grover et al. | |
| 11,369,404 B2 | 6/2022 | Hibner et al. | |
| 11,426,191 B2 | 8/2022 | Vakharia et al. | |
| 11,457,945 B2 | 10/2022 | Hunter et al. | |
| 11,471,181 B2 | 10/2022 | Hunter et al. | |
| 11,612,409 B2 | 3/2023 | Black et al. | |
| 2005/0021018 A1 | 1/2005 | Anderson et al. | |
| 2006/0079874 A1 | 4/2006 | Faller et al. | |
| 2007/0191713 A1 | 8/2007 | Eichmann et al. | |
| 2008/0200940 A1 | 8/2008 | Eichmann et al. | |
| 2014/0005681 A1* | 1/2014 | Gee | A61F 9/00745 606/130 |
| 2021/0015572 A1 | 1/2021 | Gomez et al. | |
| 2021/0022815 A1 | 1/2021 | Abbott | |
| 2021/0059709 A1 | 3/2021 | Black et al. | |
| 2021/0059711 A1 | 3/2021 | Hunter et al. | |
| 2022/0125460 A1 | 4/2022 | Black et al. | |
| 2022/0125463 A1 | 4/2022 | Black et al. | |
| 2022/0125464 A1 | 4/2022 | Black et al. | |
| 2022/0125465 A1 | 4/2022 | Beckman et al. | |
| 2022/0125466 A1 | 4/2022 | Beckman et al. | |
| 2022/0125467 A1 | 4/2022 | Black et al. | |
| 2022/0125468 A1 | 4/2022 | Scheib et al. | |
| 2022/0125469 A1 | 4/2022 | Black et al. | |
| 2022/0125470 A1 | 4/2022 | Black et al. | |
| 2022/0125471 A1 | 4/2022 | Black et al. | |
| 2022/0125472 A1 | 4/2022 | Beckman et al. | |
| 2022/0125473 A1 | 4/2022 | Black et al. | |

OTHER PUBLICATIONS

International Search Report and Written Opinion dated Mar. 25, 2022 for Application No. PCT/IB2021/059601, 23 pgs.

U.S. Appl. No. 62/930,638, filed Nov. 5, 2019, by Davison et al., titled "Articulation Joint With Helical Lumen.".

\* cited by examiner

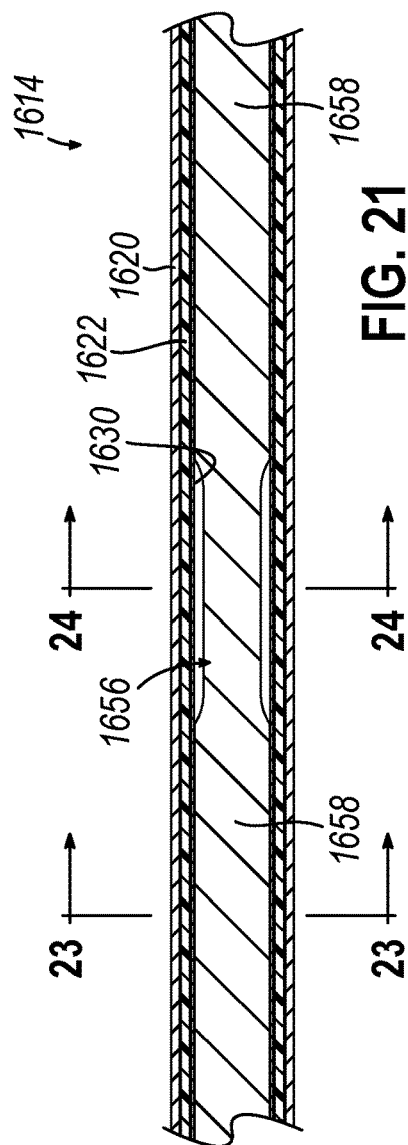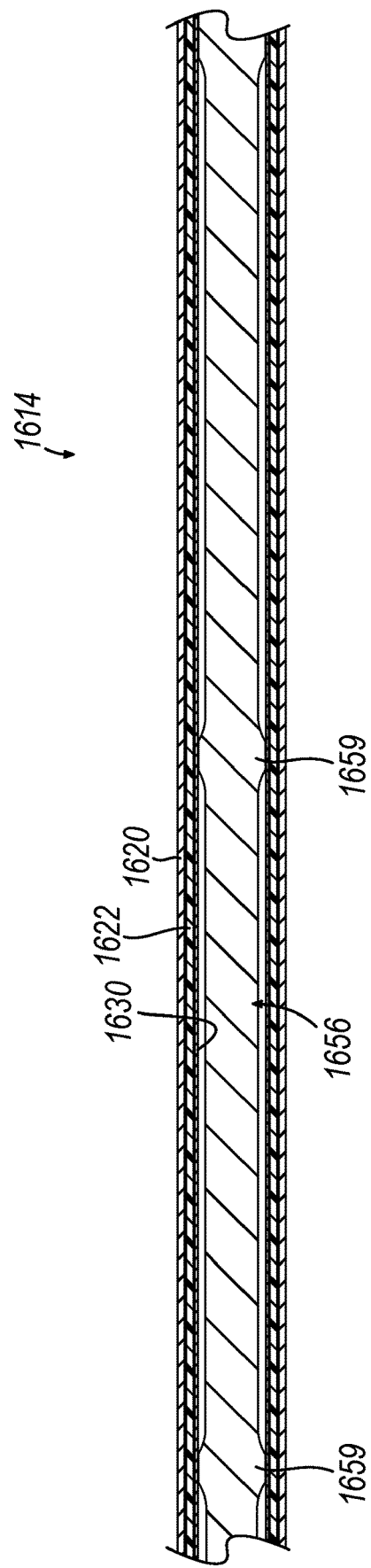

DAMPING RINGS FOR AN ULTRASONIC SURGICAL INSTRUMENT

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

In one example, the end effector of the surgical instrument includes a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; and U.S. Pub. No. 2008/0200940, entitled "Ultrasonic Device for Cutting and Coagulating," published Aug. 21, 2008, now abandoned, the disclosure of which is incorporated by reference herein.

Examples of robotic systems, at least some of which have ultrasonic features and/or associated articulatable portions, include U.S. patent application Ser. No. 16/556,661, entitled "Ultrasonic Surgical Instrument with a Multi-Planar Articulating Shaft Assembly," filed on Aug. 30, 2019, published as U.S. Pub. No. 2021/0059709 on Mar. 4, 2021, issued as U.S. Pat. No. 11,690,642 on Jul. 4, 2023; U.S. patent application Ser. No. 16/556,667, entitled "Ultrasonic Transducer Alignment of an Articulating Ultrasonic Surgical Instrument," filed on Aug. 30, 2019, issued as U.S. Pat. No. 11,612,409 on Mar. 28, 2023; U.S. patent application Ser. No. 16/556,625, entitled "Ultrasonic Surgical Instrument with Axisymmetric Clamping," filed on Aug. 30, 2019, issued as U.S. Pat. No. 11,471,181 on Oct. 18, 2022; U.S. patent application Ser. No. 16/556,635, entitled "Ultrasonic Blade and Clamp Arm Alignment Features," filed on Aug. 30, 2019, issued as U.S. Pat. No. 11,457,945 on Oct. 4, 2022; U.S. patent application Ser. No. 16/556,727, entitled "Rotatable Linear Actuation Mechanism," filed on Aug. 30, 2019, published as U.S. Pub. No. 2021/0059711 on Mar. 4, 2021, issued as U.S. Pat. No. 11,712,261 on Aug. 1, 2023; and/or U.S. patent application Ser. No. 62/930,638, entitled "Articulation Joint with Helical Lumen," filed on Nov. 5, 2019. The disclosure of each of these applications is incorporated by reference herein.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 21 depicts a cross-sectional view of the shaft assembly of FIG. 18, the cross-section taken along section line 21-21 of FIG. 18;

FIG. 22 depicts another cross-sectional view of the shaft assembly of FIG. 18, the cross-section taken along section line 22-22 of FIG. 18;

Figure 1:
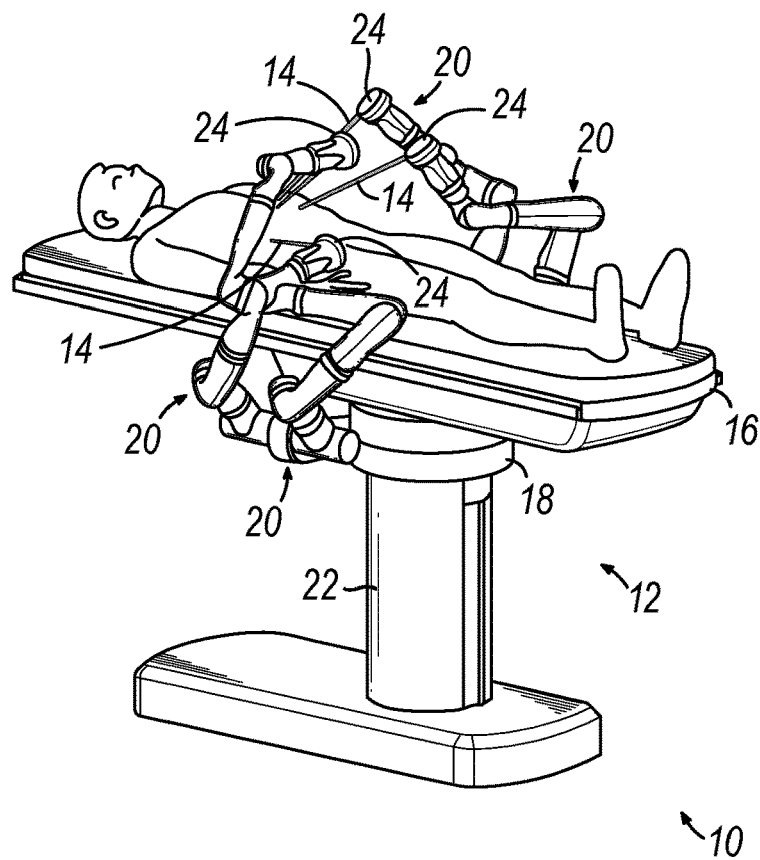
FIG. 1 depicts a perspective view of a first example of a table-based robotic system configured for a laparoscopic procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "rear," "clockwise," "counterclockwise," "longitudinal," and "transverse" also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

In addition to performing the breadth of procedures, the robotically-enabled medical system may provide additional benefits, such as enhanced imaging and guidance to assist the medical professional. Additionally, the robotically-enabled medical system may provide the medical professional with the ability to perform the procedure from an ergonomic position without the need for awkward arm motions and positions. Still further, the robotically-enabled medical system may provide the medical professional with the ability to perform the procedure with improved ease of use such that one or more of the instruments of the robotically-enabled medical system may be controlled by a single operator.

I. Exemplary Robotically-Enabled Medical System

FIG. 1 shows an exemplary robotically-enabled medical system, including a first example of a table-based robotic system (10). Table-based robotic system (10) of the present example includes a table system (12) operatively connected to an instrument for a diagnostic and/or therapeutic procedure in the course of treating a patient. Such procedures may include, but are not limited, to bronchoscopy, ureteroscopy, a vascular procedure, and a laparoscopic procedure. To this end, the instrument illustrated in the present example is an ultrasonic surgical instrument (14) configured for a laparoscopic procedure, although it will be appreciated that any instrument for treating a patient may be similarly used. At least part of table-based robotic system (10) may be constructed and operable in accordance with at least some of the teachings of any of the various patents, patent application publications, and patent applications that are cited herein. As described therein and as will be described in greater detail below, ultrasonic surgical instrument (14) is operable to cut tissue and seal or weld tissue (e.g., a blood vessel, etc.) substantially simultaneously. While one or more examples incorporates various ultrasonic features, such as ultrasonic surgical instrument (14), the invention is not intended to be unnecessarily limited to the ultrasonic features described herein.

A. First Exemplary Table-Based Robotic System

With respect to FIG. 1, table-based robotic system (10) includes table system (12) having a platform, such as a table (16), with a plurality of carriages (18) which may also be referred to herein as "arm supports," respectively supporting the deployment of a plurality of robotic arms (20). Table-based robotic system (10) further includes a support structure, such as a column (22), for supporting table (16) over the floor. Table (16) may also be configured to tilt to a desired angle during use, such as during laparoscopic procedures. Each robotic arm (20) includes an instrument driver (24) configured to removably connect to and manipulate ultrasonic surgical instrument (14) for use. In alternative examples, instrument drivers (24) may be collectively positioned in a linear arrangement to support the instrument extending therebetween along a "virtual rail" that may be repositioned in space by manipulating the one or more robotic arms (20) into one or more angles and/or positions. In practice, a C-arm (not shown) may be positioned over the patient for providing fluoroscopic imaging.

In the present example, column (22) includes carriages (18) arranged in a ring-shaped form to respectively support one or more robotic arms (20) for use. Carriages (18) may translate along column (22) and/or rotate about column (22) as driven by a mechanical motor (not shown) positioned within column (22) in order to provide robotic arms (20) with access to multiples sides of table (16), such as, for example, both sides of the patient. Rotation and translation of carriages (18) allows for alignment of instruments, such as ultrasonic surgical instrument (14) into different access points on the patient. In alternative examples, such as those discussed below in greater detail, table-based robotic system (10) may include a patient table or bed with adjustable arm supports including a bar (26) (see FIG. 2) extending alongside. One or more robotic arms (20) (e.g., via a shoulder with an elbow joint) may be attached to carriages (18), which are vertically adjustable so as to be stowed compactly beneath the patient table or bed, and subsequently raised during use.

Table-based robotic system (10) may also include a tower (not shown) that divides the functionality of table-based robotic system (10) between table (16) and the tower to reduce the form factor and bulk of table (16). To this end, the tower may provide a variety of support functionalities to table (16), such as processing, computing, and control capabilities, power, fluidics, and/or optical and sensor processing. The tower may also be movable so as to be positioned away from the patient to improve medical professional access and de-clutter the operating room. The tower may also include a master controller or console that provides both a user interface for operator input, such as keyboard and/or pendant, as well as a display screen, including a touchscreen, for pre-operative and intra-operative information, including, but not limited to, real-time imaging, navigation, and tracking information. In one example, the tower may include gas tanks to be used for insufflation.

B. Second Exemplary Table-Based Robotic System

Figure 2:
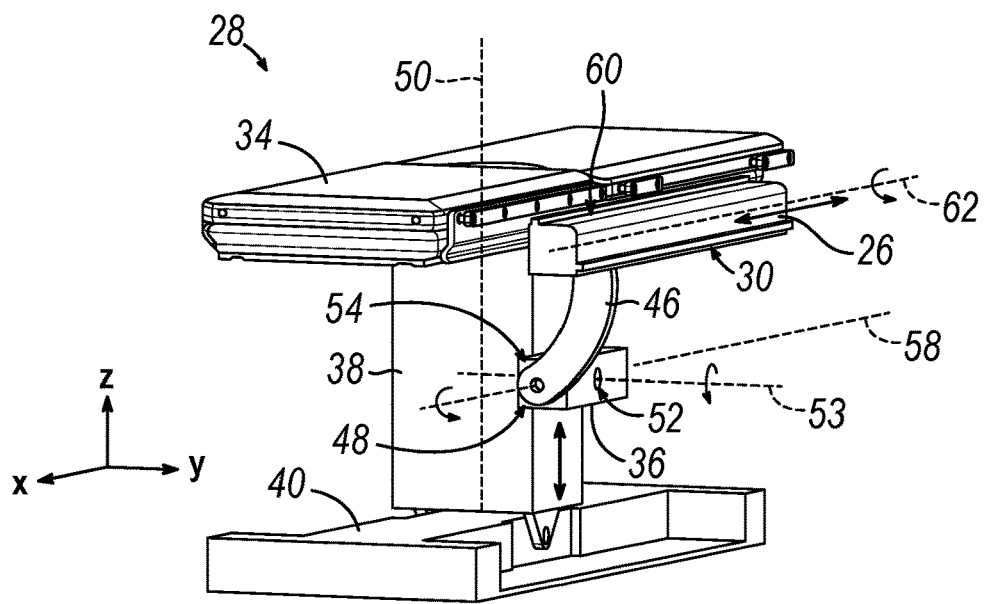
FIG. 2 depicts a perspective view of a second example of a table-based robotic system.
Figure 3:
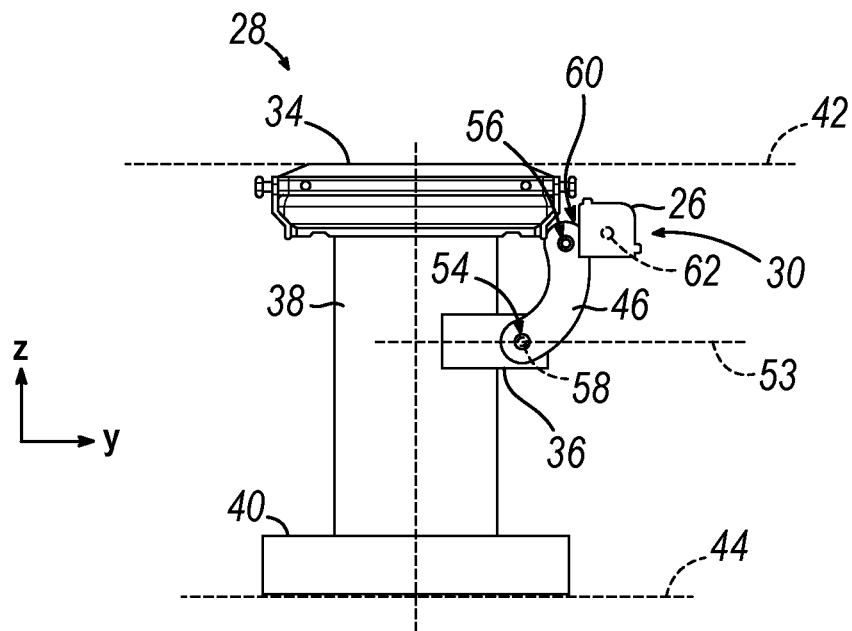
FIG. 3 depicts an end elevational view of the table-based robotic system of FIG. 2.
Figure 4:
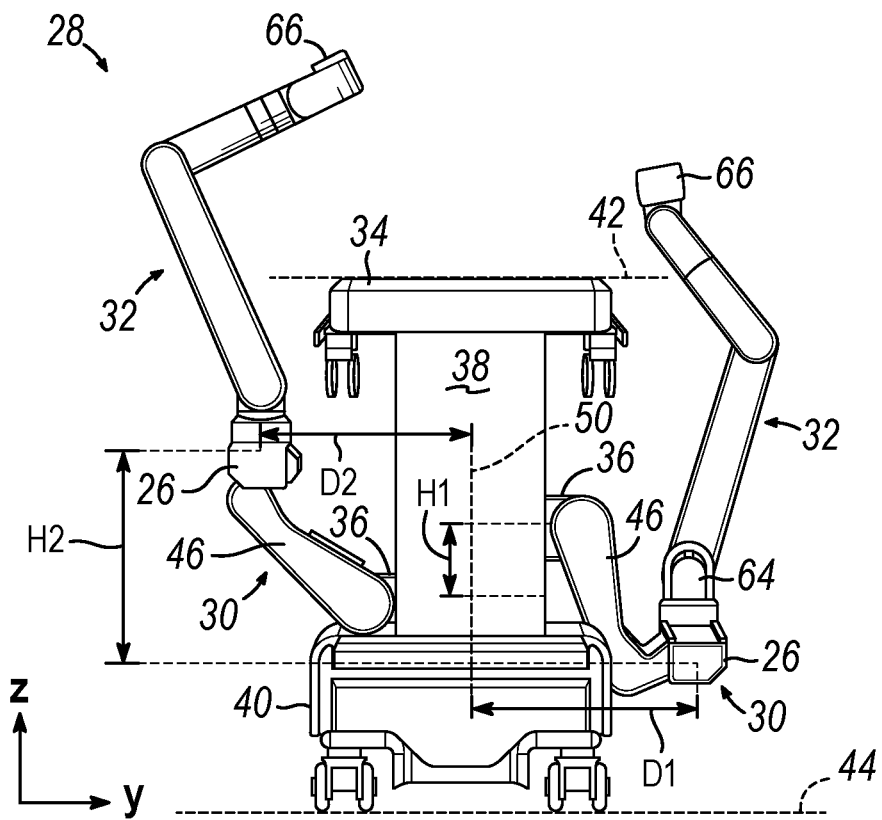
FIG. 4 depicts the end elevational view of the table-based robotic system of FIG. 3 including a pair of exemplary robotic arms.

As discussed briefly above, a second exemplary table-based robotic system (28) includes one or more adjustable arm supports (30) including bars (26) configured to support one or more robotic arms (32) relative to a table (34) as shown in FIGS. 2-4. In the present example, a single and a pair of adjustable arm supports (30) are shown, though additional arm supports (30) may be provided about table (34). Adjustable arm support (30) is configured to selectively move relative to table (34) so as to alter the position of adjustable arm support (30) and/or any robotic arms (32) mounted thereto relative to table (34) as desired. Such adjustable arm supports (30) provide high versatility to table-based robotic system (28), including the ability to easily stow one or more adjustable arm supports (30) with robotic arms (32) beneath table (34).

Each adjustable arm support (30) provides several degrees of freedom, including lift, lateral translation, tilt, etc. In the present example shown in FIGS. 2-4, arm support (30) is configured with four degrees of freedom, which are illustrated with arrows. A first degree of freedom allows adjustable arm support (30) to move in the z-direction ("Z-lift"). For example, adjustable arm support (30) includes a vertical carriage (36) configured to move up or down along or relative to a column (38) and a base (40) supporting table (34). A second degree of freedom allows adjustable arm support (30) to tilt about an axis extending in the y-direction. For example, adjustable arm support (30) includes a rotary joint, which allows adjustable arm support (30) to align the bed in a Trendelenburg position. A third degree of freedom allows adjustable arm support (30) to "pivot up" about an axis extending in the x-direction, which may be useful to adjust a distance between a side of table (34) and adjustable arm support (30). A fourth degree of freedom allows translation of adjustable arm support (30) along a longitudinal length of table (34), which extends along the x-direction. Base (40) and column (38) support table (34) relative to a support surface, which is shown along a support axis (42) above a floor axis (44) and in the present example. While the present example shows adjustable arm support (30) mounted to column (38), arm support (30) may alternatively be mounted to table (34) or base (40).

As shown in the present example, adjustable arm support (30) includes vertical carriage (36), a bar connector (46), and bar (26). To this end, vertical carriage (36) attaches to column (38) by a first joint (48), which allows vertical carriage (36) to move relative to column (38) (e.g., such as up and down a first, vertical axis (50) extending in the z-direction). First joint (48) provides the first degree of freedom ("Z-lift") to adjustable arm support (30). Adjustable arm support (30) further includes a second joint (52), which provides the second degree of freedom (tilt) for adjustable arm support (30) to pivot about a second axis (53) extending in the y-direction. Adjustable arm support (30) also includes a third joint (54), which provides the third degree of freedom ("pivot up") for adjustable arm support (30) about a third axis (58) extending in the x-direction. Furthermore, an additional joint (56) mechanically constrains third joint (54) to maintain a desired orientation of bar (26) as bar connector (46) rotates about third axis (58). Adjustable arm support (30) includes a fourth joint (60) to provide a fourth degree of freedom (translation) for adjustable arm support (30) along a fourth axis (62) extending in the x-direction.

With respect to FIG. 4, table-based robotic system (28) is shown with two adjustable arm supports (30) mounted on opposite sides of table (34). A first robotic arm (32) is attached to one such bar (26) of first adjustable arm support (30). First robotic arm (32) includes a base (64) attached to bar (26). Similarly, second robotic arm (32) includes base (64) attached to other bar (26). Distal ends of first and second robotic arms (32) respectively include instrument drivers (66), which are configured to attach to one or more instruments such as those discussed below in greater detail.

In one example, one or more robotic arms (32) has seven or more degrees of freedom. In another example, one or more robotic arms (32) has eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (64) (1-degree of freedom including translation). In one example, the insertion degree of freedom is provided by robotic arm (32), while in another example, such as ultrasonic surgical instrument (14) (see FIG. 6A), the instrument includes an instrument-based insertion architecture.

Figure 5:
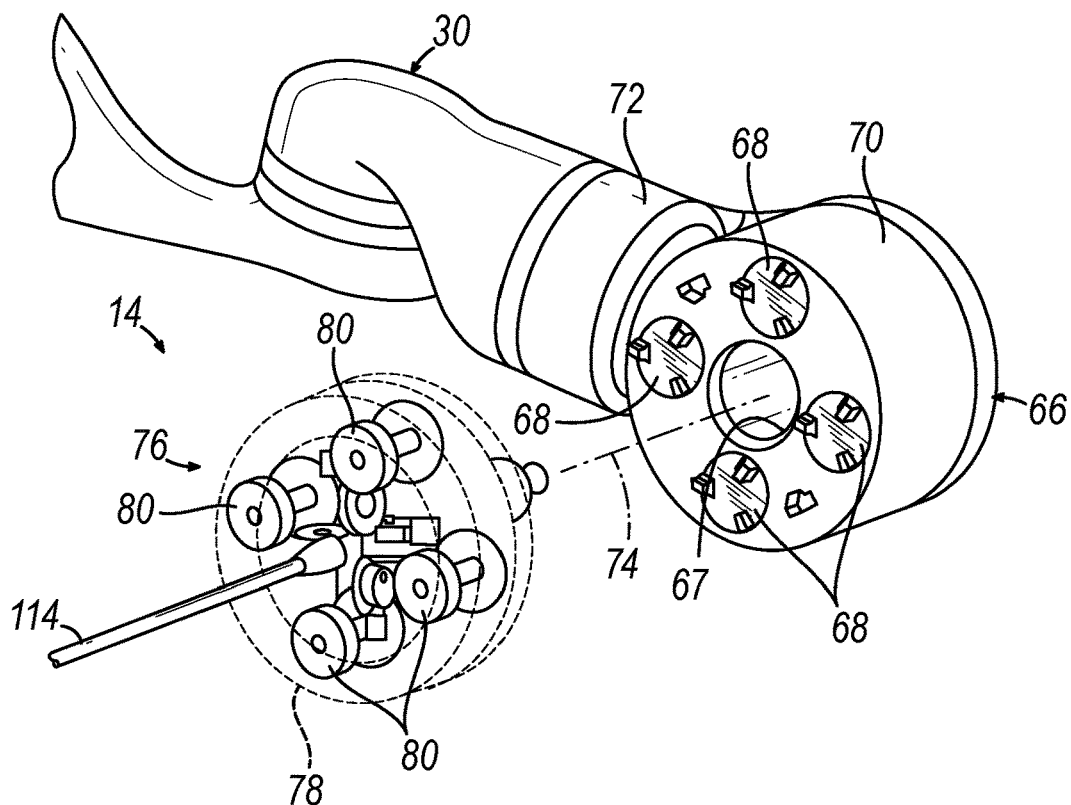
FIG. 5 depicts a partially exploded perspective view of the robotic arm of FIG. 4 having an instrument driver and a first exemplary surgical instrument.

FIG. 5 shows one example of instrument driver (66) in greater detail with ultrasonic surgical instrument (14) removed therefrom. Given the present instrument-based insertion architecture shown with reference to ultrasonic surgical instrument (14), instrument driver (66) further includes a clearance bore (67) extending entirely therethrough so as to movably receive a portion of ultrasonic surgical instrument (14) as discussed below in greater detail. Instrument driver (66) may also be referred to herein as an "instrument drive mechanism," an "instrument device manipulator," or an "advanced device manipulator" (ADM). Instruments may be designed to be detached, removed, and interchanged from instrument driver (66) for individual sterilization or disposal by the medical professional or associated staff. In some scenarios, instrument drivers (66) may be draped for protection and thus may not need to be changed or sterilized.

Each instrument driver (66) operates independently of other instrument drivers (66) and includes a plurality of rotary drive outputs (68), such as four drive outputs (68), also independently driven relative to each other for directing operation of ultrasonic surgical instrument (14). Instrument driver (66) and ultrasonic surgical instrument (14) of the present example are aligned such that the axes of each drive output (68) are parallel to the axis ultrasonic surgical instrument (14). In use, control circuitry (not shown) receives a control signal, transmits motor signals to desired motors (not shown), compares resulting motor speed as measured by respective encoders (not shown) with desired speeds, and modulates motor signals to generate desired torque at one or more drive outputs (68).

In the present example, instrument driver (66) is circular with respective drive outputs (68) housed in a rotational assembly (70). In response to torque, rotational assembly (70) rotates along a circular bearing (not shown) that connects rotational assembly (70) to a non-rotational portion (72) of instrument driver (66). Power and controls signals may be communicated from non-rotational portion (72) of instrument driver (66) to rotational assembly (70) through electrical contacts therebetween, such as a brushed slip ring connection (not shown). In one example, rotational assembly (70) may be responsive to a separate drive output (not shown) integrated into non-rotatable portion (72), and thus not in parallel to the other drive outputs (68). In any case, rotational assembly (70) allows instrument driver (66) to rotate rotational assembly (70) and drive outputs (68) in conjunction with ultrasonic surgical instrument (14) as a single unit around an instrument driver axis (74).

Any systems described herein, including table-based robotic system (28), may further include an input controller (not shown) for manipulating one or more instruments. In some embodiments, the input controller (not shown) may be coupled (e.g., communicatively, electronically, electrically, wirelessly and/or mechanically) with an instrument such that manipulation of the input controller (not shown) causes a corresponding manipulation of the instrument e.g., via master slave control. In one example, one or more load cells (not shown) may be positioned in the input controller such that portions of the input controller (not shown) are capable of operating under admittance control, thereby advantageously reducing the perceived inertia of the controller while in use.

In addition, any systems described herein, including table-based robotic system (28) may provide for non-radiation-based navigational and localization means to reduce exposure to radiation and reduce the amount of equipment within the operating room. As used herein, the term "localization" may refer to determining and/or monitoring the position of objects in a reference coordinate system. Technologies such as pre-operative mapping, computer vision, real-time electromagnetic sensor (EM) tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

C. First Exemplary Ultrasonic Surgical Instrument

Figure 6A:
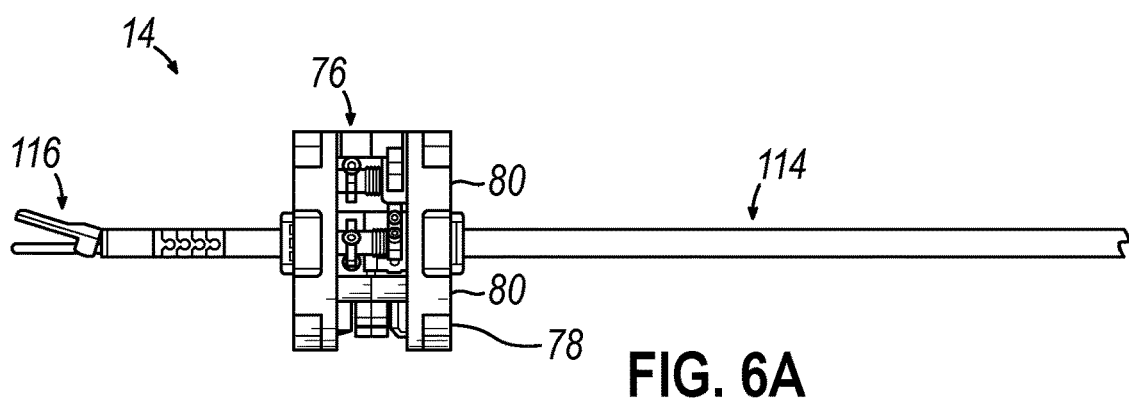
FIG. 6A depicts a side elevational view of the surgical instrument of FIG. 5 in a retracted position.
Figure 6B:
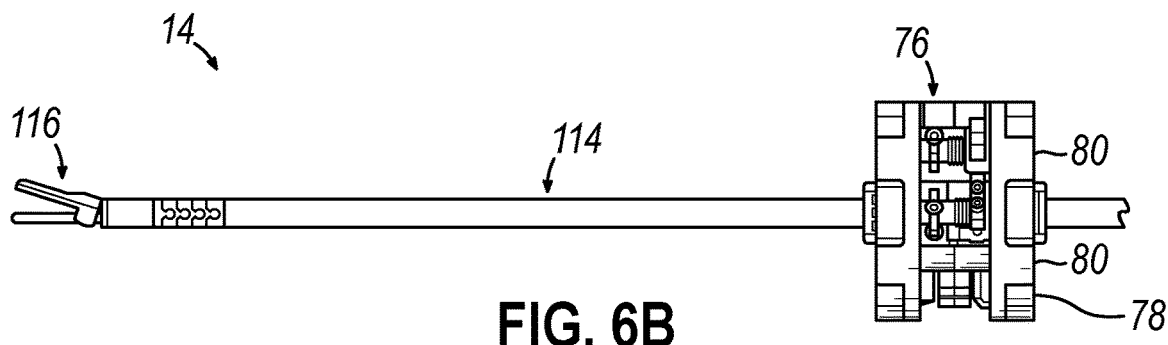
FIG. 6B depicts the side elevational view the surgical instrument similar to FIG. 6A, but in an extended position.

With respect to FIGS. 5-6B and in cooperation with instrument driver (66) discussed above, ultrasonic surgical instrument (14) includes the elongated shaft assembly (114) and an instrument base (76) with an attachment interface (78) having a plurality of drive inputs (80) configured to respectively couple with corresponding drive outputs (68). Shaft assembly (114) of ultrasonic surgical instrument (14) extends from a center of base (76) with an axis substantially parallel to the axes of the drive inputs (80) as discussed briefly above. With shaft assembly (114) positioned at the center of base (76), shaft assembly (114) is coaxial with instrument driver axis (74) when attached and movably received in clearance bore (67). Thus, rotation of rotational assembly (70) causes shaft assembly (114) of ultrasonic surgical instrument (14) to rotate about its own longitudinal axis while clearance bore (67) provides space for translation of shaft assembly (114) during use.

To this end, FIGS. 5-6B show ultrasonic surgical instrument (14) having the instrument-based insertion architecture as discussed briefly above. Ultrasonic surgical instrument (14) includes elongated shaft assembly (114), the end effector (116) connected to and extending distally from shaft assembly (114), and instrument base (76) coupled to shaft assembly (114). Notably, insertion of shaft assembly (114) is grounded at instrument base (76) such that end effector (116) is configured to selectively move longitudinally from a retracted position to an extended position, vice versa, and any desired longitudinal position therebetween. As used herein, the retracted position is shown in FIG. 6A and places end effector (116) relatively close and proximally toward instrument base (76), whereas the extended position is shown in FIG. 6B and places end effector (116) relatively far and distally away from instrument base (76). Insertion into and withdrawal of end effector (116) relative to the patient may thus be facilitated by ultrasonic surgical instrument (14), although it will be appreciated that such insertion into and withdrawal may also occur via adjustable arm supports (30) in one or more examples.

While the present example of instrument driver (66) shows drive outputs (68) arranged in rotational assembly (70) so as to face in a distal direction like distally projecting end effector (116) from shaft assembly (114), an alternative instrument driver (not shown) may include drive output (68) arranged on an alternative rotational assembly (70) to face in a proximal direction, opposite of the distally projecting end effector (116). In such an example, ultrasonic surgical instrument (14) may thus have drive inputs (80) facing distally to attach to instrument drivers (66) facing proximally in an opposite direction from that shown in FIG. 5. The invention is thus not intended to be unnecessarily limited to the particular arrangement of drive outputs (68) and drive inputs (80) shown in the present example and any such arrangement for operatively coupling between drive outputs and inputs (68, 80) may be similarly used.

While various features configured to facilitate movement between end effector (116) and drive inputs (80) are described herein, such features may additionally or alternatively include pulleys, cables, carriers, such as a kinetic articulating rotating tool (KART), and/or other structures configured to communicate movement along shaft assembly (114). Moreover, while instrument base (76) is configured to operatively connect to instrument driver (66) for driving various features of shaft assembly (114) and/or end effector (116) as discussed below in greater detail, it will be appreciated that alternative examples may operatively connect shaft assembly (114) and/or end effector (116) to an alternative handle assembly (not shown). Such handle assembly (not shown) may include a pistol grip (not shown) in one example, configured to be directly gripped and manipulated by the medical professional for driving various features of shaft assembly (114) and/or end effector (116). The invention is thus not intended to be unnecessarily limited to use with instrument driver (66).

i. First Exemplary End Effector and Acoustic Drivetrain

Figure 7A:
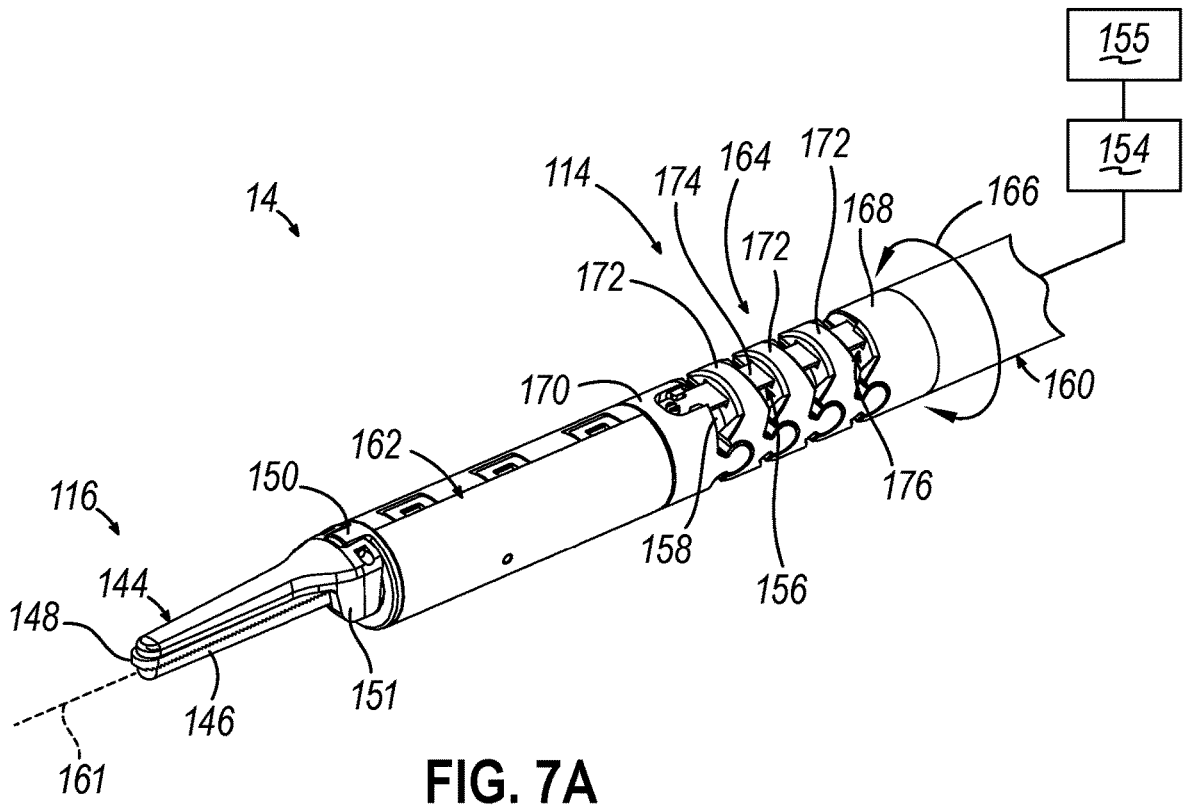
FIG. 7A depicts an enlarged perspective view of the surgical instrument of FIG. 6A with an end effector in a closed position and a shaft assembly in a straight configuration.
Figure 7B:
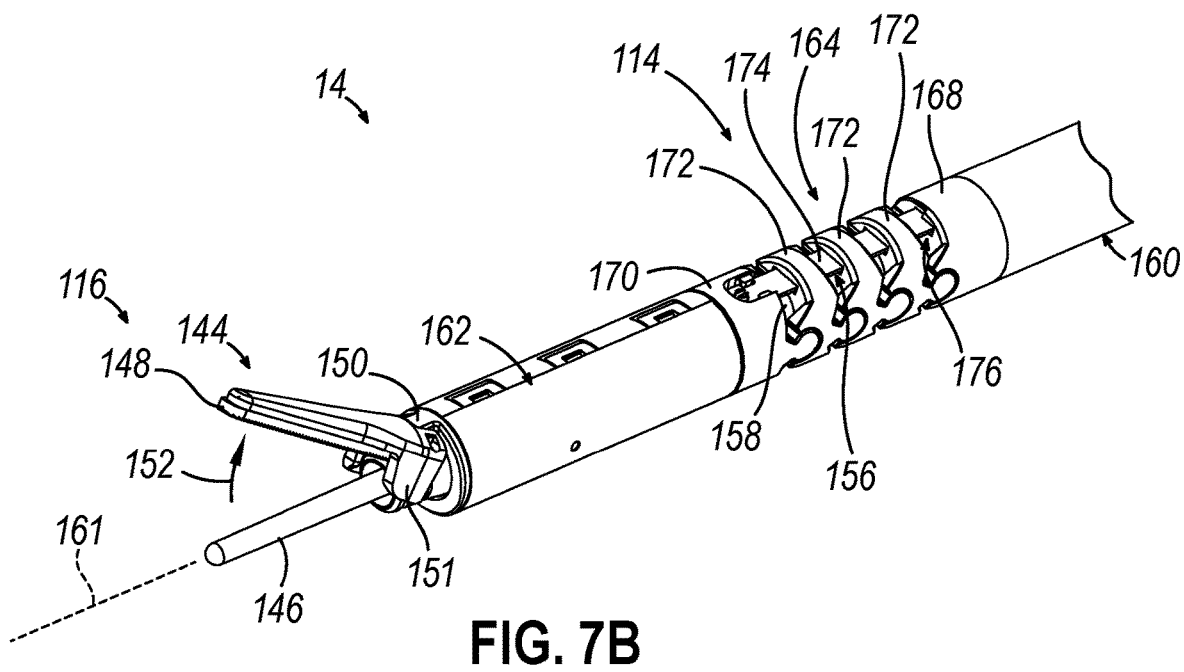
FIG. 7B depicts the enlarged perspective view of the surgical instrument similar to FIG. 7A, but showing the end effector in an open position.

As best seen in FIGS. 7A-7B, end effector (116) of the present example includes a clamp arm (144) and an ultrasonic blade (146). Clamp arm (144) has a clamp pad (148) secured to an underside of clamp arm (144), facing blade (146). Clamp arm (144) is pivotally secured to a distally projecting tongue (150) of shaft assembly (114). Clamp arm (144) is operable to selectively pivot toward and away from blade (146) to selectively clamp tissue between clamp arm (144) and blade (146). A pair of arms (151) extend transversely from clamp arm (144) and are pivotally secured to another portion of shaft assembly (114) configured to longitudinally slide to pivot clamp arm (144) as indicated by an arrow (152) between a closed position shown in FIG. 7A and an open position shown in FIG. 7B.

Blade (146) of the present example is operable to vibrate at ultrasonic frequencies in order to effectively cut through and seal tissue, particularly when the tissue is being compressed between clamp pad (148) and blade (146). Blade (146) is positioned at a distal end of an acoustic drivetrain. This acoustic drivetrain includes a transducer assembly (154) and an acoustic waveguide (156), which includes a flexible portion (158) discussed below in greater detail.

Transducer assembly (154) is further connected to a generator (155) of the acoustic drivetrain. More particularly, transducer assembly (154) is coupled with generator (155) such that transducer assembly (154) receives electrical power from generator (155). Piezoelectric elements (not shown) in transducer assembly (154) convert that electrical power into ultrasonic vibrations. By way of example only, generator (155) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein.

When transducer assembly (154) of the present example is activated, mechanical oscillations are transmitted through waveguide (156) to reach blade (146), thereby providing oscillation of blade (146) at a resonant ultrasonic frequency (e.g., 55.5 kHz). Thus, when tissue is secured between blade (146) and clamp pad (148), the ultrasonic oscillation of blade (146) may simultaneously sever the tissue and denature the proteins in adjacent tissue cells, thereby providing a coagulative effect with relatively little thermal spread.

ii. First Exemplary Shaft Assembly and Articulation Section

As shown in FIGS. 7A-7B, shaft assembly (114) includes a proximal shaft portion (160) extending along a longitudinal axis (161), a distal shaft portion (162) distally projecting relative to proximal shaft portion (160), and an articulation section (164) extending between proximal and distal shaft portions (160, 162). Shaft assembly (114) is configured to rotate about longitudinal axis (161) as indicated by an arrow (166). In one example, shaft assembly (114) rotates in the clockwise or counterclockwise directions completely around longitudinal axis (161) and may be selectively fixed in any rotational position about longitudinal axis (161) for positioning articulation section (164) and/or end effector (116) about longitudinal axis (161).

Articulation section (164) is configured to selectively position end effector (116) at various lateral deflection angles relative to longitudinal axis (161) defined by proximal shaft portion (160). Articulation section (164) may take a variety of forms. In the present example, articulation section (164) includes a proximal link (168), a distal link (170), and a plurality of intermediate links (172) connected in series between proximal and distal links (168, 170). Articulation section (164) further includes a pair of articulation bands (174) extending along a pair of respective channels (176) collectively defined through links (168, 170, 172). Links (168, 170, 172) are generally configured to pivot relative to each other upon actuation of articulation bands (174) to thereby bend articulation section (164) with flexible portion (158) of waveguide (156) therein to achieve an articulated state.

Figure 8A:
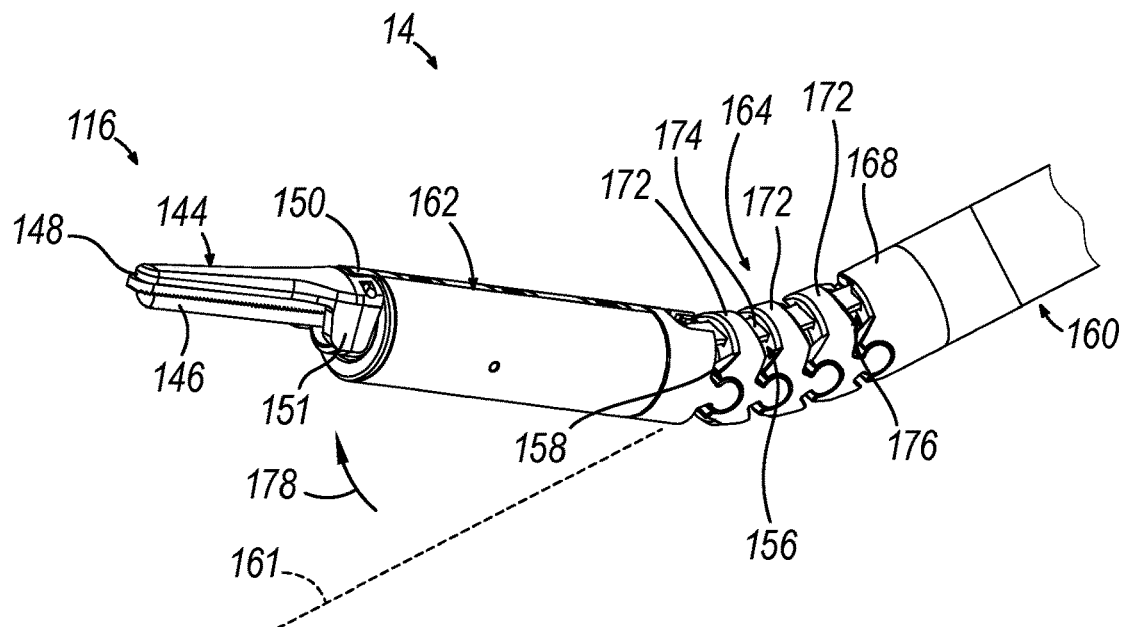
FIG. 8A depicts an enlarged perspective view of the surgical instrument of FIG. 6A with the end effector in a closed position and the shaft assembly in a first articulated configuration.
Figure 8B:
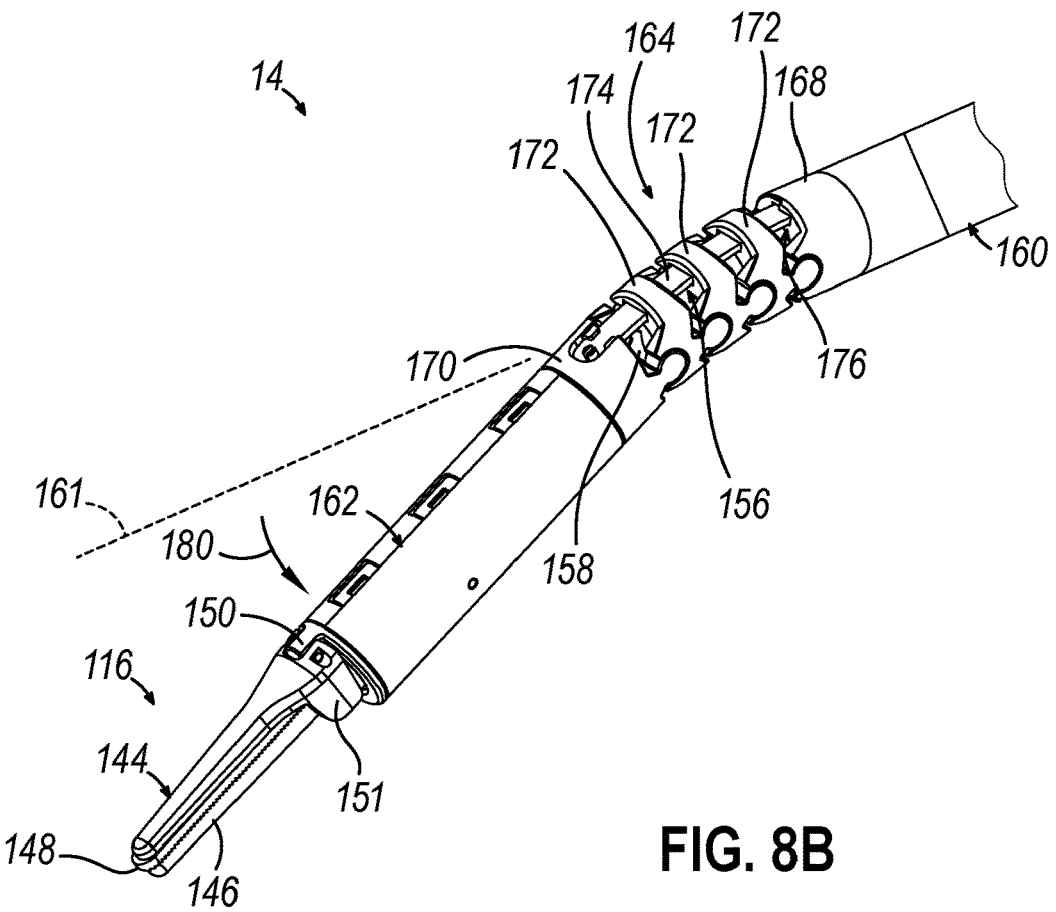
FIG. 8B depicts the enlarged perspective view of the surgical instrument similar to FIG. 8A, but with the shaft assembly in a second articulated configuration.

Links (168, 170, 172) shown in FIGS. 7B-8B pivotally interlock to secure distal shaft portion (162) relative to proximal shaft portion (160) while allowing for deflection of distal shaft portion (162) relative to longitudinal axis (161). Thus, as a pair of articulation bands (174) translate longitudinally in an opposing fashion, this will cause articulation section (164) to bend via links (168, 170, 172) thereby laterally deflecting end effector (116) away from the longitudinal axis (161) of proximal shaft portion (160) from a straight configuration as shown in FIG. 7B to a first articulated configuration as shown in FIG. 8A and indicated by an arrow (178) or a second articulated configuration as shown in FIG. 8B and indicated by an arrow (180). Furthermore, flexible acoustic waveguide (156) is configured to effectively communicate ultrasonic vibrations from waveguide (156) to blade (146) even when articulation section (164) is in an articulated configuration as shown in FIGS. 8A-8B.

II. Exemplary Alternative Ultrasonic Surgical Instrument

In some instances, it may be desirable to use various alternative ultrasonic surgical instruments with robotic systems (10, 28) described above in addition to, or in lieu of, instrument (14) described above. Such alternative ultrasonic surgical instruments may be desirable to provide improved operability when used with robotic systems (10, 28). For instance, as described above, instrument (14) may move between a retracted positioned and an extended position. With such a feature, it may be desirable to modify components similar to waveguide (156) and/or blade (146) to provide enhanced functionality. Additionally, as also described above, use of rotational assembly (70) of robotic arm (20, 32) may enable rotation of an entire instrument rather than specific structures of the instrument being rotatable. This functionality may permit alternative configurations related to structures similar to waveguide (156), blade (146), and/or transducer assembly (154). Although various suitable features associated with structures similar to waveguide (156), blade (146), and/or etc. are described herein in specific configurations and in combination with specific devices, it should be understood that in other examples such features may be arranged in other configurations and with other devices.

Figure 9:
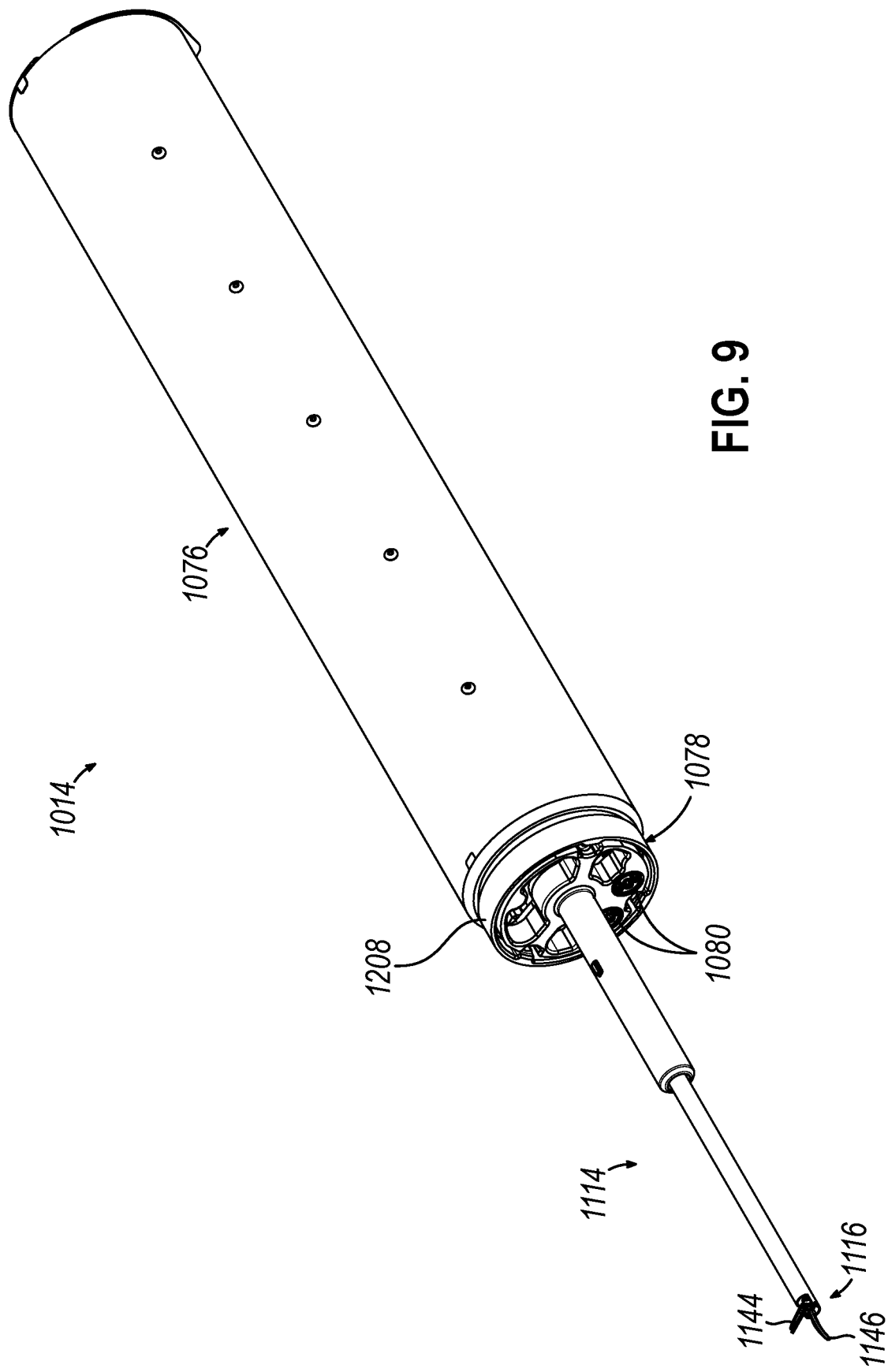
FIG. 9 depicts a perspective view of a second exemplary surgical instrument.

FIG. 9 depicts an exemplary alternative ultrasonic surgical instrument (1014) configured for use with robotic systems (10, 28) described above. It should be understood that ultrasonic surgical instrument (1014) of the present example is substantially similar to ultrasonic surgical instrument (14) described above, except where otherwise explicitly noted herein. For instance, similar to ultrasonic surgical instrument (14) described above, ultrasonic surgical instrument (1014) of the present example includes an instrument base (1076) having an attachment interface (1078) with a plurality of drive inputs (1080) facing distally and configured to engage proximally facing drive outputs (68) of a robotic arm (not shown). As with attachment interface (78) described above, attachment interface (1078) of the present example includes drive inputs (1080) configured to respectively couple with corresponding drive outputs (68). As will be described in greater detail below, such drive inputs (1080) are generally configured to move, actuate, and/or drive various components of ultrasonic surgical instrument (1014).

Also like ultrasonic surgical instrument (14) described above, ultrasonic surgical instrument (1014) of the present example includes a shaft assembly (1114) that is configured to extend from a center of base (1076) with an axis substantially parallel to the axes of the drive inputs (1080). With shaft assembly (1114) positioned at the center of base (1076), shaft assembly (1114) is coaxial with ultrasonic surgical instrument driver axis (74) when attached. Thus, rotation of rotational assembly (70) is configured to cause shaft assembly (1114) of ultrasonic surgical instrument (1014) to rotate about its own longitudinal axis. In other words, it should be understood that ultrasonic surgical instrument (1014) is configured to be rotated similar to that of rotational assembly (70) of robotic arm (32) such that individual components of ultrasonic surgical instrument (1014) (e.g., shaft assembly (1114)) do not need to rotate independently of other portions of ultrasonic surgical instrument (1014).

As also with ultrasonic surgical instrument (14), ultrasonic surgical instrument (1014) of the present example includes the instrument-based insertion architecture described above. To this end, shaft assembly (1114) includes an end effector (1116) on a distal end thereof. To facilitate such instrument-based insertion, insertion of shaft assembly (1114) is grounded at instrument base (1076) such that end effector (1116) is configured to selectively move longitudinally from a retracted position to an extended position, vice versa, and any desired longitudinal position therebetween. As used herein, the retracted position is shown in FIG. 9 and places end effector (1116) relatively close and proximally toward instrument base (1076), whereas the extended position places end effector (1116) relatively far and distally away from instrument base (1076). Insertion into and withdrawal of end effector (1116) relative to the patient may thus be facilitated by ultrasonic surgical instrument (1014), although it will be appreciated that such insertion into and withdrawal may also occur similar to robotic arms (32) in one or more examples.

As also with ultrasonic surgical instrument (114) described above, ultrasonic surgical instrument (1014) of the present example includes an end effector (1116) substantially similar to end effector (116) described above. For instance, like end effector (116), end effector (1116) of the present example includes a clamp arm (1144) and an ultrasonic blade (1146). As with clamp arm (144) described above, clamp arm (1144) can include a clamp pad (not shown) similar to clamp pad (148) described above. Similarly, clamp arm (1144) is pivotally secured to shaft assembly (1114) by a distally projecting tongue (not shown) similar to tongue (150) described above. Thus, clamp arm (1144) is operable to selectively pivot toward and away from blade (1146) to selectively clamp tissue between the clamp arm and blade (1146).

Blade (1146) of the present example is operable to vibrate at ultrasonic frequencies in order to effectively cut through and seal tissue, particularly when the tissue is being compressed between the clamp pad and blade (1146). As such, blade (1146) is positioned at a distal end of an acoustic drivetrain. This acoustic drivetrain includes a transducer assembly (1154) and an acoustic waveguide (1156) (see FIG. 12), discussed in greater detail below.

Although not shown, it should be understood that in some examples shaft assembly (1114) may include structures similar to articulation section (164) described above. As noted above, such structures may permit shaft assembly (1114) to bend or articulate at a predetermined point to promote greater flexibility in positioning shaft assembly (1114) within a patient. Of course, such structures for articulation of shaft assembly (1114) are merely optional and may be omitted in some examples.

Figure 10:
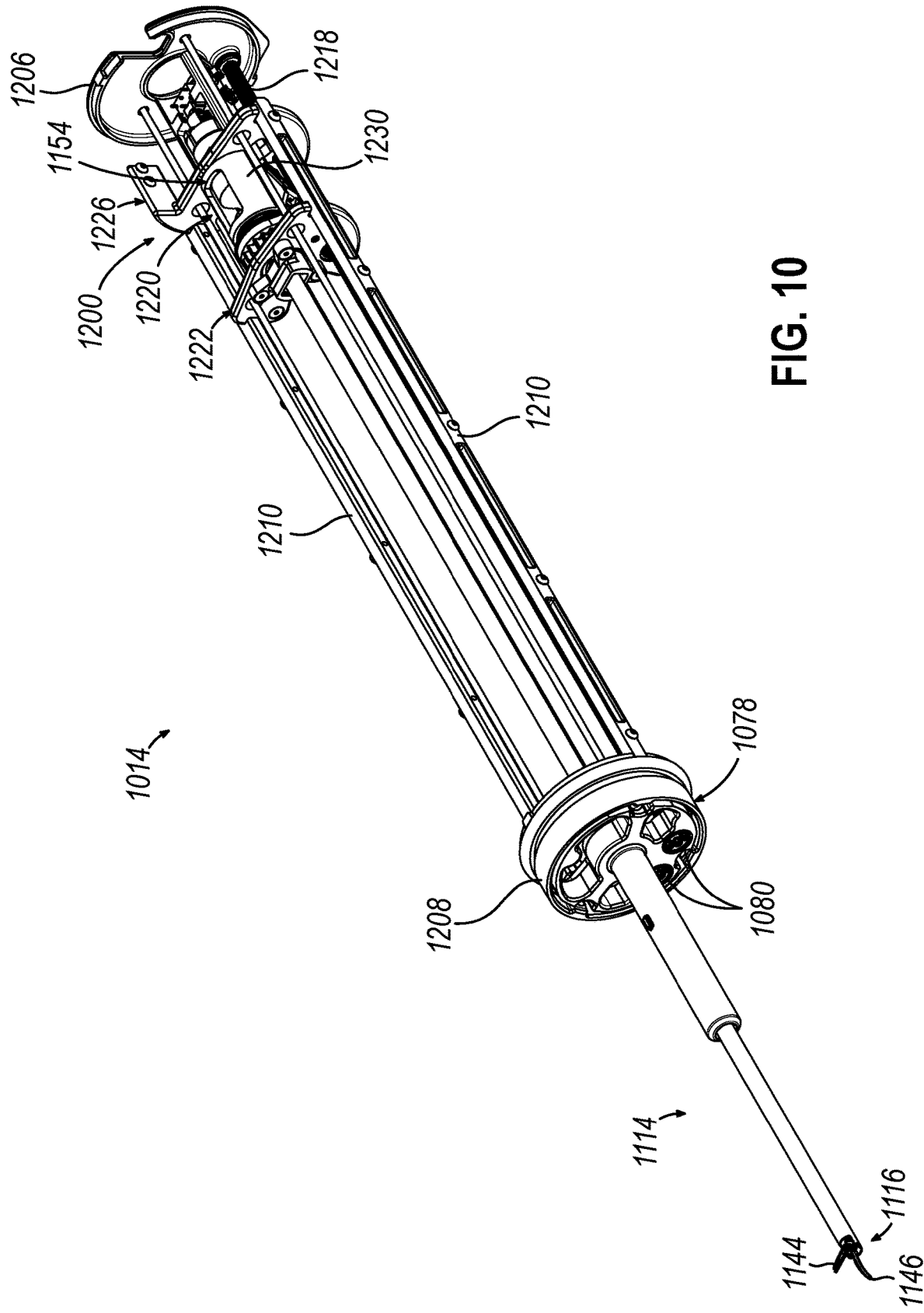
FIG. 10 depicts another perspective view of the surgical instrument of FIG. 9, the second surgical instrument having a housing removed.

As best seen in FIG. 10, ultrasonic surgical instrument (1014) includes various drive components configured to move shaft assembly (1114) between the retracted position and the extended position. As similarly described above with respect to ultrasonic surgical instrument (14), while ultrasonic surgical instrument (1014) may use various features configured to facilitate movement between end effector (1116) and drive inputs (1080)), such features may additionally or alternatively include pulleys, cables, carriers, such as a kinetic articulating rotating tool (KART), and/or other structures configured to communicate movement along shaft assembly (1114). Moreover, while instrument base (1076) is configured to operatively connect to one or more instrument drivers (66) for driving various features of shaft assembly (1114) and/or end effector (1116), as discussed below in greater detail, it will be appreciated that alternative examples may operatively connect shaft assembly (1114) and/or end effector (1116) to an alternative handle assembly (not shown). Such handle assembly (not shown) may include a pistol grip (not shown) in one example, configured to be directly gripped and manipulated by the medical professional for driving various features of shaft assembly (1114) and/or end effector (1116). The invention is thus not intended to be unnecessarily limited to use with one or more instrument drivers (66).

Figure 11A:
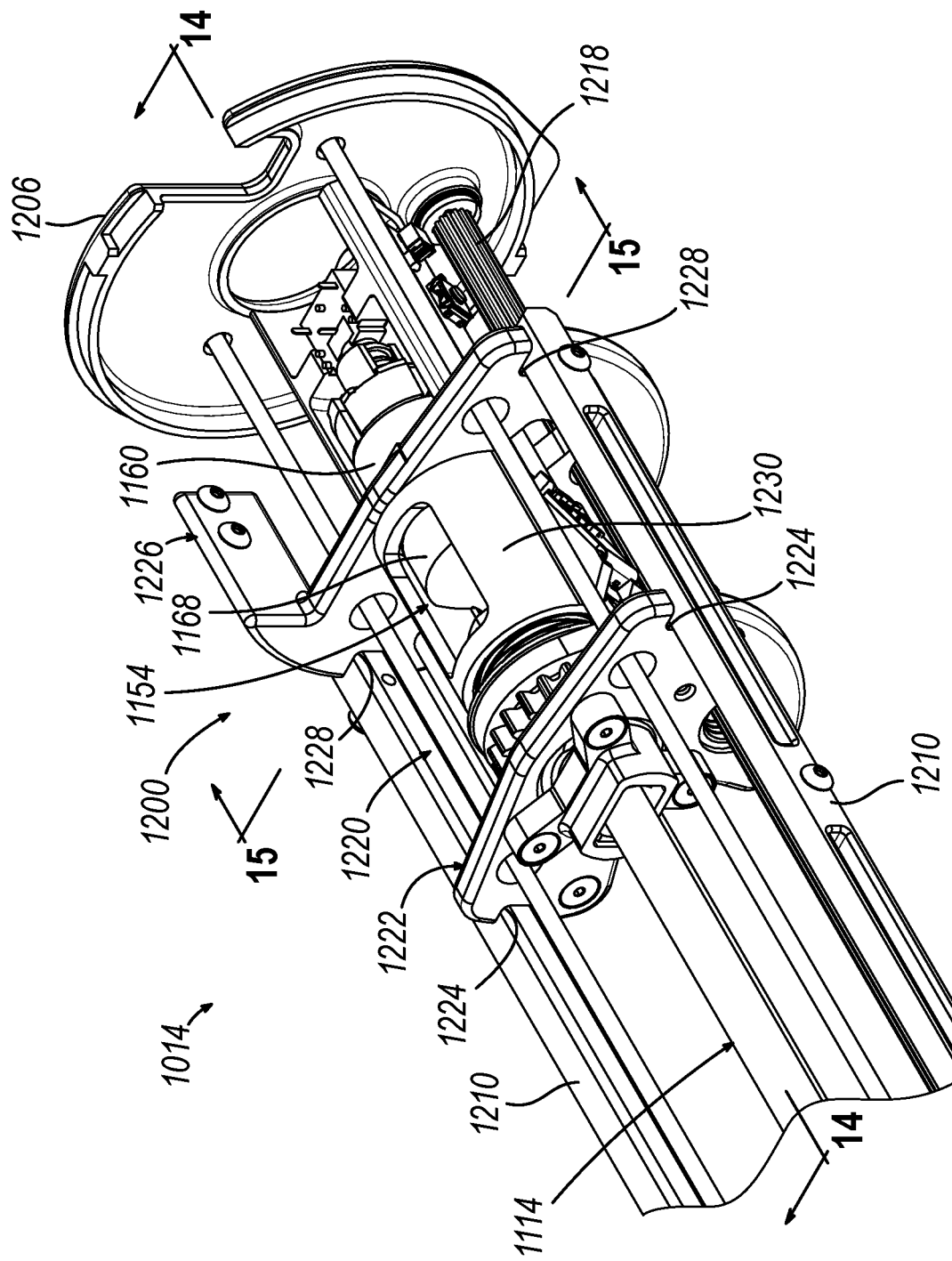
FIG. 11A depicts a detailed perspective view of a proximal end portion of the surgical instrument of FIG. 9.
Figure 11B:
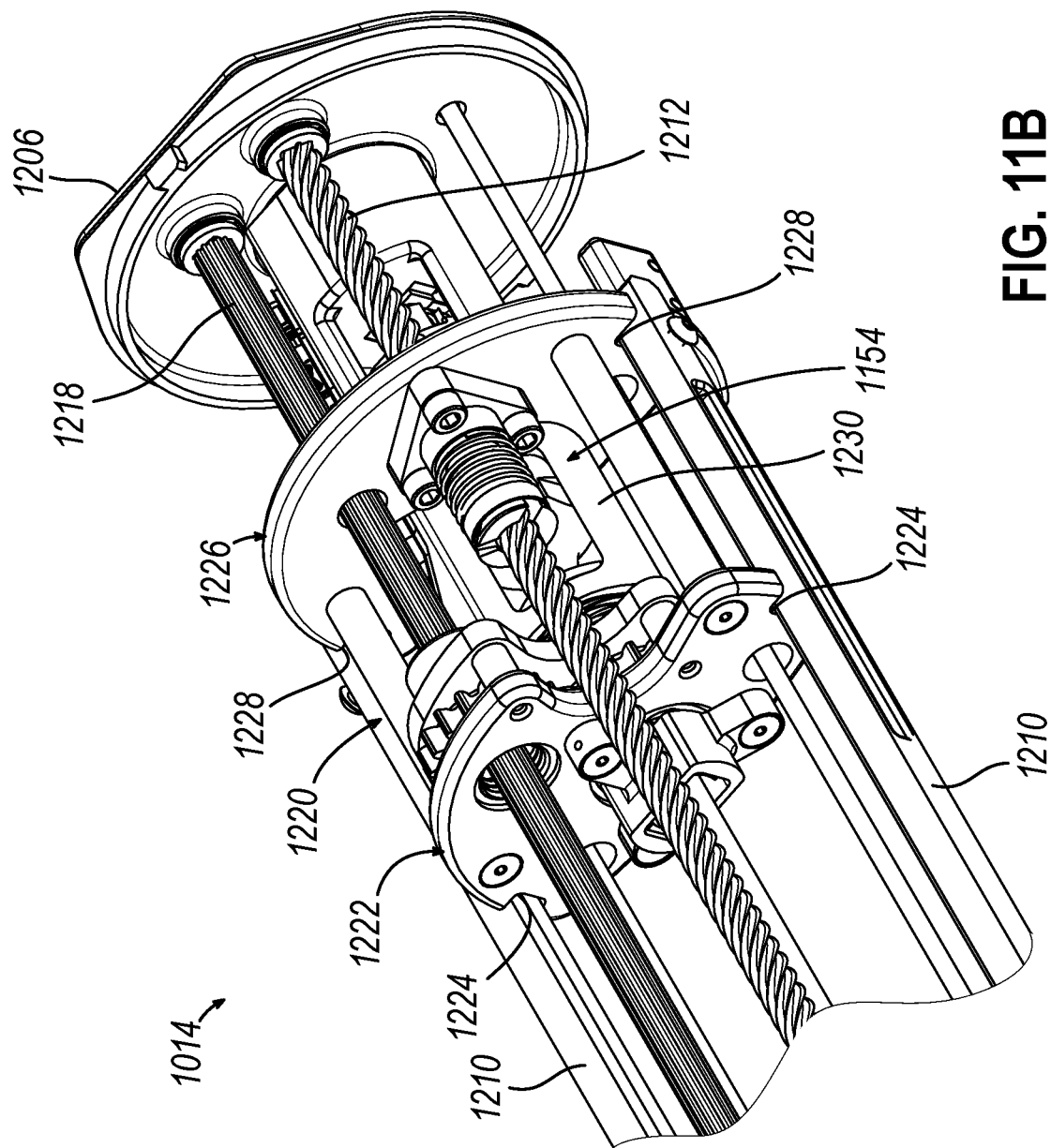
FIG. 11B depicts another detailed perspective view of the proximal end portion of the surgical instrument of FIG. 9.

As best seen in FIGS. 10 through 11B, the interior of ultrasonic surgical instrument (1014) includes a carrier (1200) having one or more guide rails (1210), a translation driver (1212), an actuation driver (1218) and a carriage (1220). In the present example, the combination of the guide rails (1210), translation driver (1212), actuation driver (1218), and carriage (1220) may collectively and more particularly be referred to as a KART or a carrier KART, although it will be appreciated that any features configured to movably support one or more portions of the acoustic drivetrain may generally be referred as "carrier" such that the term "carrier" is not intended to unnecessarily limit the invention to specific aspects of the KART herein. Guide rails (1210) extend axially between a proximal end portion (1206) and a distal end portion (1208) and in some contexts may be supported by an outer housing of ultrasonic surgical instrument (1014). As will be discussed in greater detail below, guide rails (1210) are generally configured to guide or otherwise direct movement of carriage (1220) along a predetermined axial path. To facilitate this functionality, guide rails (1210) of the present example are generally configured as elongate rails having square or rectangular cross-section. However, it should be understood that in other examples, guide rails (1210) may take on a variety of elongate rail forms such as cylindrical, C-shaped, I-shaped, and/or etc.

Translation driver (1212), as best seen in FIG. 11B, also extends between each end portion (1206, 1208) and is rotatable about a longitudinal axis thereof. Although not shown, it should be understood that the distal end of translation driver (1212) is in communication with a respective driver input (1080) oriented on, or proximate to, attachment interface (1078). This permits a corresponding drive output (68) of robotic arm (32) to communicate rotary motion from robotic arm (32) to translation driver (1212).

Translation driver (1212) is generally configured to drive translation of carriage (1220) by rotation of translation driver (1212) using drive output (68) of robotic arm (32). In the present example, translation driver (1212) is a lead screw, which may also be referred to as a leadscrew, configured to engage with one or more threaded components associated with carriage (1220) to thereby convert rotary motion of translation driver (1212) into translation of carriage (1220). Thus, translation driver (1212) may be configured with one or more threads in some examples. Although a lead screw is used in the present example, it should be understood that in other examples various alternative configurations of translation driver (1212) can be used in addition to or in lieu of the lead screw. Suitable alternative configurations may include components such as cable and pully combinations, gears, linear actuators, fluid or pneumatically actuated pistons, and/or etc.

Actuation driver (1218) is generally configured to selectively drive various portions of ultrasonic surgical instrument (1014) from one or more drive outputs (68) of robotic arm (32). For instance, in the present example, actuation driver (1218) is configured as an elongate spur gear configured to drive rotation of various components within carriage (1220) as carriage (1220) is moved using translation driver (1212). In the present example, the rotation provided by actuation driver (1218) is used to actuate end effector (1116) between an open position and a closed position, as will be described in greater detail below. As such, it should be understood that actuation driver (1218) can be associated with additional drive components such as gears, cams, links, cranks, lead screws, and the like to drive movement of end effector (1116) using rotary input provided by actuation driver (1218). Although actuation driver (1218) is described herein as being configured to selectively drive movement of end effector (1116), it should be understood that in other examples, actuation driver (1218) can be used to drive other suitable components of ultrasonic surgical instrument (1014). In addition, or in the alternative, in some examples, multiple actuation drivers (1218) can be used to drive multiple components of ultrasonic surgical instrument (1014) independently. Of course, various alternative applications of actuation driver (1218) will be apparent to those of ordinary skill in the art in view of the teachings herein.

Carriage (1220) is positioned between guide rails (1210) such that carriage (1220) is generally configured to move axially along guide rails (1210) under the influence of translation driver (1212). Carriage (1220) includes a distal guide (1222), a proximal guide (1226), and a transducer housing (1230) extending distally from proximal guide (1226). Both distal guide (1222) and proximal guide (1226) include a plurality of guide slots (1224, 1228) configured to receive guide rails (1210). Thus, distal guide (1222) and proximal guide (1226) are both configured to confine movement of carriage (1220) along the path defined by guide rails (1210) via guide slots (1224, 1228). Although guide slots (1224, 1228) in the present example are configured as slots corresponding to the shape of guide rails (1210), it should be understood that in other examples alternative forms of engagement between distal guide (1222), proximal guide (1226), and guide rails (1210) may be used. For instance, in some examples guide rails (1210) may include one or more slots or channels, while distal guide (1222) and proximal guide (1226) may include one or more protrusions configured for receipt into such slots or channels. Of course, various other forms of engagement may be used as will be apparent to those of ordinary skill in the art in view of the teachings herein.

Transducer housing (1230) comprises a generally hollow cylindrical shape integral with, and extending distally from, proximal guide (1226). As will be described in greater detail below, transducer housing (1230) is generally configured to receive a portion of transducer assembly (1154). As will also be described in greater detail below, transducer housing (1230) and/or portions of proximal guide (1226) are generally configured to act as a ground for transducer assembly (1154) relative to ultrasonic surgical instrument (1014). Thus, it should be understood that transducer housing (1230) and/or portions of proximal guide (1226) are generally configured to fix movement of transducer assembly (1154) relative to carriage (1220).

Figure 12:
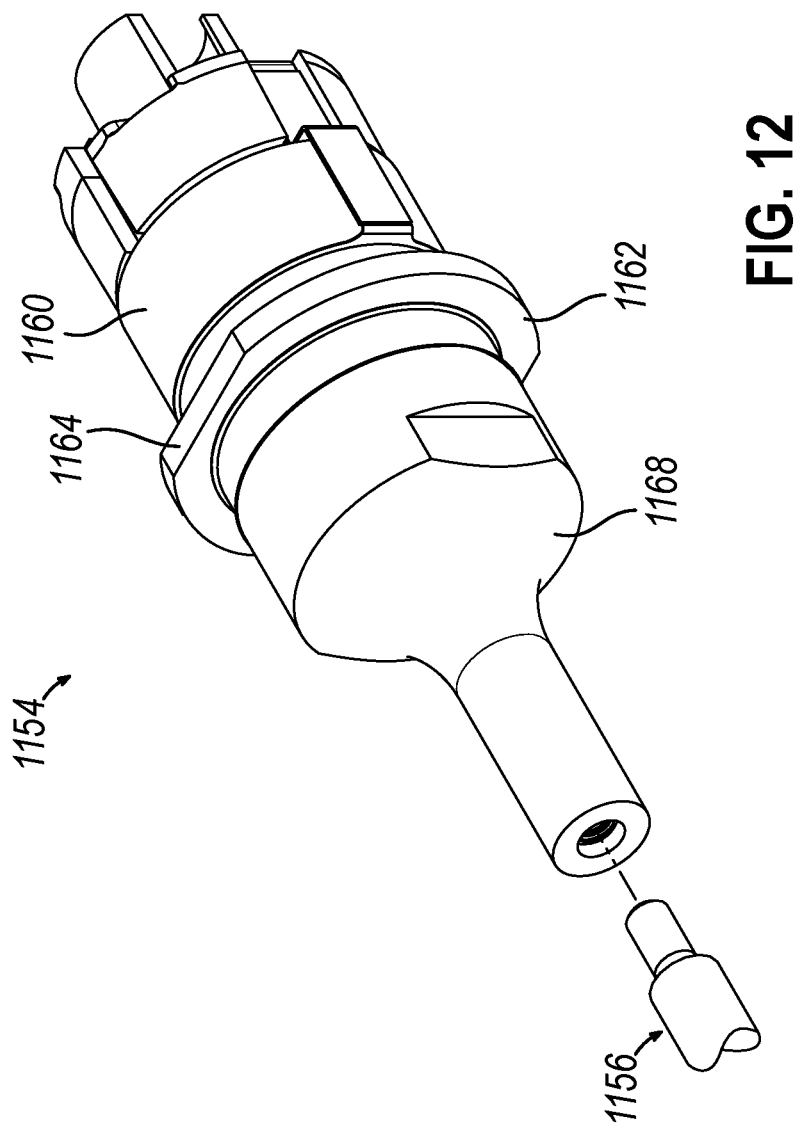
FIG. 12 depicts a perspective view of a transducer assembly of the surgical instrument of FIG. 9.

Transducer assembly (1154) is shown in greater detail in FIG. 12. Transducer assembly (1154) of the present example is substantially similar to transducer assembly (154) described above. For instance, as with transducer assembly (154), transducer assembly (1154) of the present example may be connected to a generator (not shown) similar to generator (155) of the acoustic drivetrain. Thus, the generator can be used to apply electric power to transducer assembly (1154) to activate piezoelectric elements (not shown) in transducer assembly (1154) and thereby convert the electrical power into ultrasonic vibrations. By way of example only, as with generator (154) described above, suitable generators may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein.

Transducer assembly (1154) of the present example includes a transducer body (1160) housing the piezoelectric elements, an attachment flange (1162), and a horn (1168). Attachment flange (1162) (also referred to as a fixation member herein) extends outwardly from transducer body (1160) defining a generally circular shape interrupted by one or more engagement portions, such as flats (1164). As will be described in greater detail below, flange (1162) is generally configured to engage portions of transducer housing (1230) and/or proximal guide (1226) to fixedly secure transducer assembly (1154) to carriage (1220).

Horn (1168) extends distally from transducer body (1160) and is generally configured to direct and/or amplify ultrasonic energy emitted by the piezoelectric elements of transducer body (1160) into acoustic waveguide (1156). Thus, it should be understood that waveguide (1156) may be secured to the distal end of horn (1168) in the present example. Although horn (1168) of the present example is shown as having a tapered conical shape, it should be understood that in other examples horn (1168) may take on a variety of forms.

As noted above and discussed with respect to FIG. 13, blade (1146) of the present example is operable to vibrate at ultrasonic frequencies in order to effectively cut through and seal tissue. As such, blade (1146) is positioned at a distal end of the acoustic drivetrain. As discussed above, the acoustic drivetrain includes transducer assembly (1154) and acoustic waveguide (1156).

Figure 13:
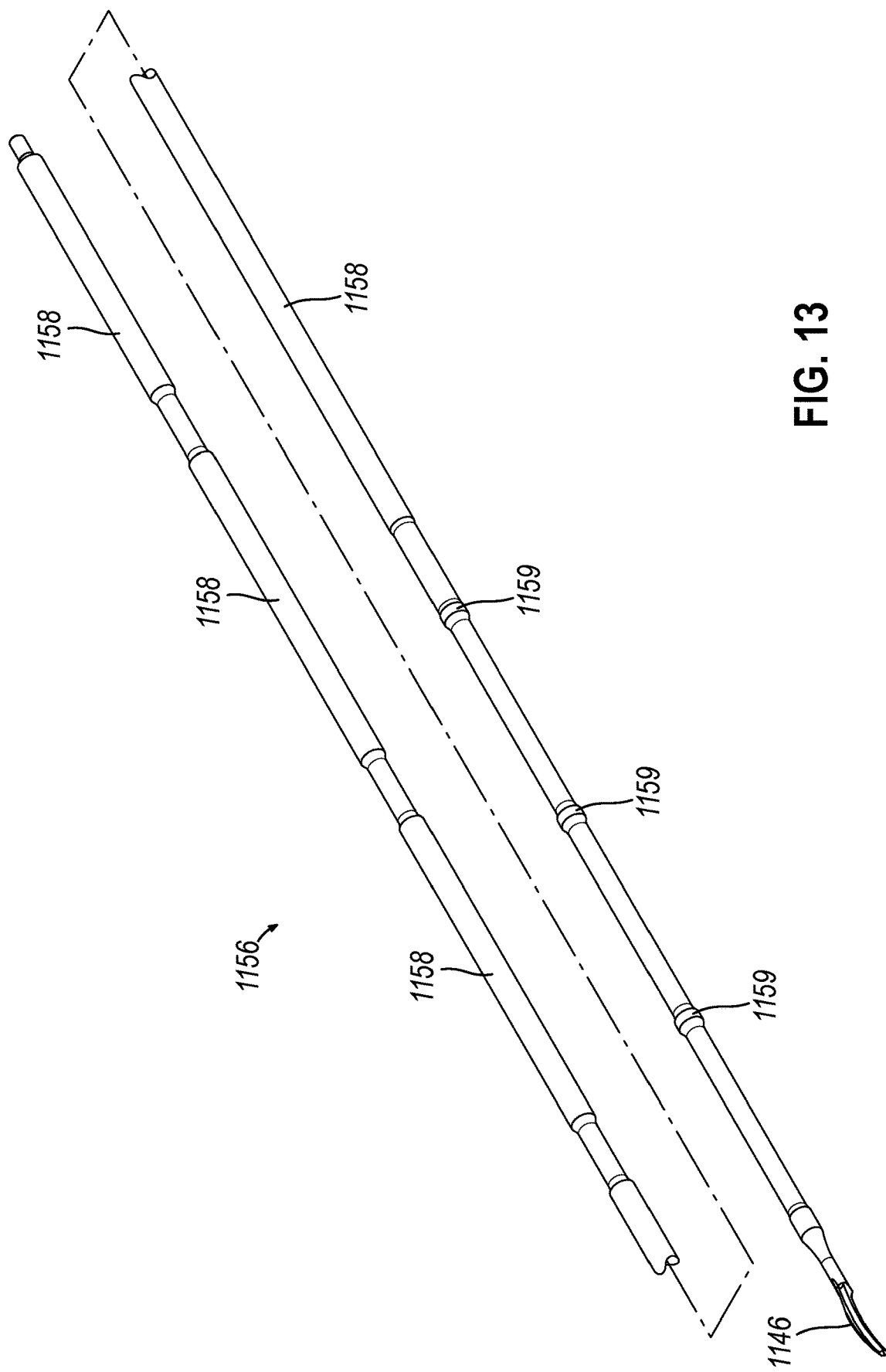
FIG. 13 depicts s perspective view of an acoustic waveguide of the surgical instrument of FIG. 9.

Acoustic waveguide (1156) is shown in greater detail in FIG. 13. As can be seen, acoustic waveguide (1156) comprises a generally elongate cylindrical structure with blade (1146) disposed on the distal end thereof. The particular length of acoustic waveguide (1156) is relatively long in comparison to lengths that may be used in other ultrasonic surgical instruments. The particular length for acoustic waveguide (1156) shown is generally configured to promote movement of shaft assembly (1114) (see FIG. 10) between the retracted position and the extended position. Although a variety of suitable lengths can be used, acoustic waveguide (1156) may be approximately 5 inches longer than other acoustic waveguides. Such an increase in length may result in certain structural changes to acoustic waveguide (1156), blade (1146), and/or transducer assembly (1154), as will be described in greater detail below.

As noted below, acoustic waveguide (1156) comprises a generally cylindrical shape. In the present example, this generally cylindrical shape is interrupted by a plurality of damping structures (1158) and a plurality of isolation structures (1159). Damping structures (1158) are generally defined by relatively thick (or increased cylindrical diameter) elongate sections of acoustic waveguide (1156). Each damping structure (1158) is positioned adjacent to an acoustical node of acoustic waveguide (1156) such that the length of each damping structure (1158) generally extends between two acoustical nodes. This positioning and the general thickness or diameter of each damping structure (1158) is generally configured to provide damping of undesirable transverse vibrations during use of acoustic waveguide (1156).

Isolation structures (1159) are generally configured to isolate acoustic waveguide (1156) and/or blade (1146) from other portions of shaft assembly (1114). Each isolation structure (1159) is positioned at an acoustical node of acoustic waveguide (1156) to reduce interference with ultrasonic energy being transmitted through waveguide (1156). In the present example, each isolation structure (1159) is formed by an overmold of material onto the outer surface of acoustic waveguide (1156). Suitable materials for such an overmold may be, for example, silicon, polymer, and/or etc. Alternatively, in some examples, the structure of acoustic waveguide (1156) itself may be configured to increase in diameter to form each isolation structure (1159).

Figure 14:
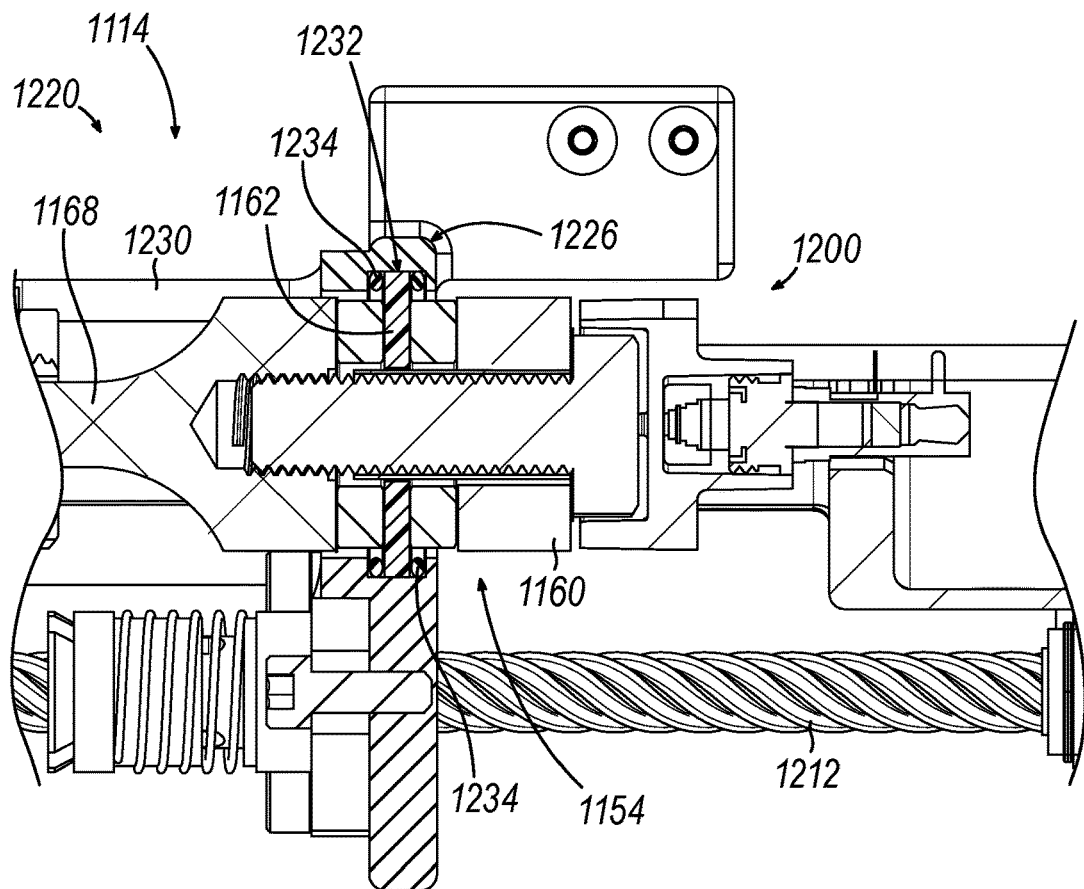
FIG. 14 depicts a cross-sectional view of the surgical instrument of FIG. 9, the cross-section taken along section line 14-14 of FIG. 11A.
Figure 15:
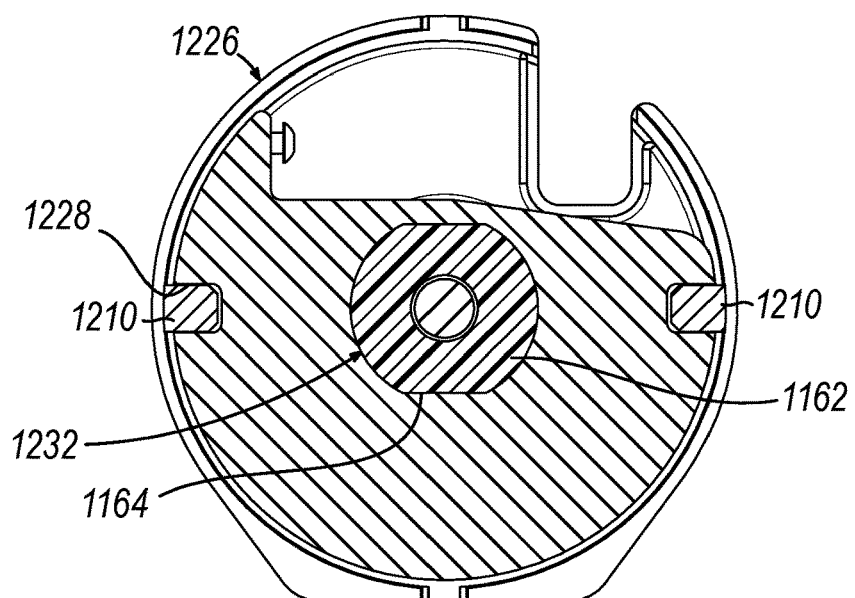
FIG. 15 depicts another cross-sectional view of the surgical instrument of FIG. 9, the cross-section taken along section line 15-15 of FIG. 11A.

FIGS. 14 and 15 show an exemplary fixation of the acoustic drivetrain within ultrasonic surgical instrument (1114). In the present example, such fixation is generally provided by only fixation of transducer assembly (1154) as opposed to other components such as acoustic waveguide (1156) and/or blade (1146). For instance, as can be seen in FIG. 14, the interior of transducer housing (1230) and/or proximal guide (1226) includes a flange receiving channel (1232) configured to receive flange (1162) of transducer assembly (1154). The interior of flange receiving channel (1232) may also optionally include one or more isolation compression rings (1234). Isolation compression rings (1234) are generally configured to engage flange (1162) to exert pressure on flange (1162) to thereby hold flange (1162) in position or otherwise stabilize transducer assembly (1154). In some examples, isolation compression rings (1234) may be further configured with damping properties to acoustically isolate transducer assembly (1154) relative to transducer housing (1230). Flange receiving channel (1232), either in combination with isolation compression rings (1234) or without isolation compression rings (1234), is generally configured to fixedly secure transducer assembly (1154) within transducer housing (1230). In other words, flange receiving channel (1232) is generally configured to provide a mechanical ground for transducer assembly (1154), which can provide stability for blade (1146) and/or acoustic waveguide (1156) without the need for other fixation structures (e.g., pins though blade (1146) and/or acoustic waveguide (1156)).

The fixation provided by flange receiving channel (1232) is both axial and rotational. For instance, as seen in FIG. 14, receipt of flange (1162) within flange receiving channel (1232) provides axial fixation by preventing movement of transducer assembly (1154) distally, proximally, and transversely (e.g., right, left, up, down, etc.) relative to flange receiving channel (1232). Meanwhile, as can be seen in FIG. 15, the cross-sectional shape of flange receiving channel (1232) is shaped to engage each flat (1164) of flange (1162), thereby fixing the rotational position of transducer assembly (1154) relative to flange receiving channel (1232). Although the present example is shown has using a channel and flange combination to fix or mechanically ground transducer assembly (1154), it should be understood that in other examples, various alternative structures for relative fixation can be used. For instance, in some examples, transducer assembly (1154) can be screwed or bolted to transducer housing (1230). In other examples, a press or compression fit can be used between transducer assembly (1154) and transducer housing (1230). In still other examples, various alternative structures for fixation may be used as will be apparent to those of ordinary skill in the art in view of the teachings herein.

Figure 16:
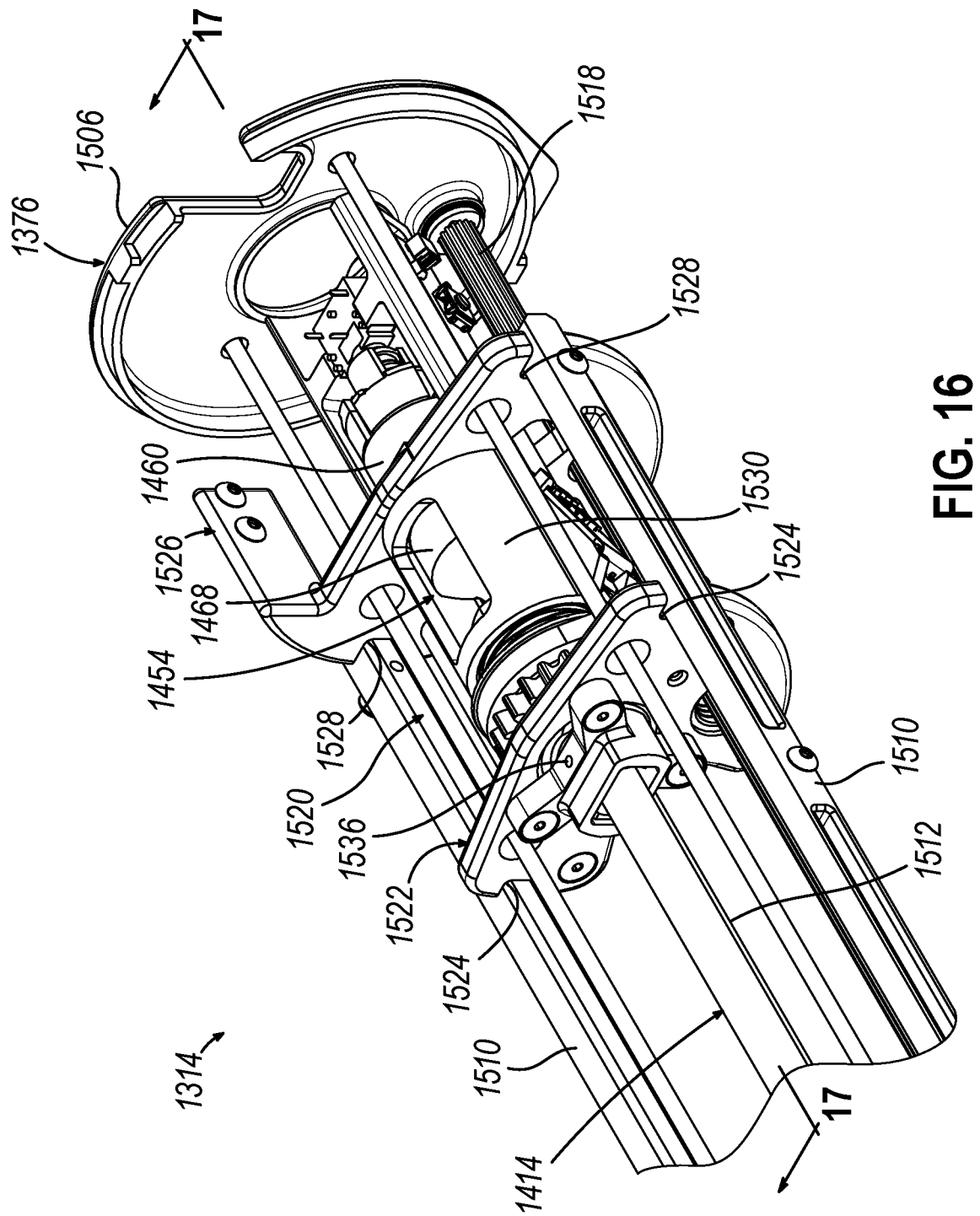
FIG. 16 depicts a detailed perspective view of a proximal end portion of a third exemplary surgical instrument.

FIG. 16 shows an exemplary alternative ultrasonic surgical instrument (1314) that is substantially similar to ultrasonic surgical instrument (1014) described above. For instance, like with ultrasonic surgical instrument (1014) described above, ultrasonic surgical instrument (1314) of the present example includes an instrument base (1376) having a proximal end portion (1506) and a longitudinally opposite attachment interface (1078) (see FIG. 9) configured to engage robotic arm (32). As similarly described above, attachment interface (1078) (see FIG. 9) of the present example includes a plurality of drive inputs (1080) (see FIG. 9) configured to respectively couple with corresponding drive outputs (68) of robotic arm (32). As will be described in greater detail below, such drive inputs (1080) (see FIG. 9) are generally configured to move, actuate, and/or drive various components of ultrasonic surgical instrument (1314).

Also like ultrasonic surgical instrument (1014) described above, ultrasonic surgical instrument (1314) of the present example includes a shaft assembly (1414) that is configured to extend from a center of base (1376) with an axis substantially parallel to the axes of the drive inputs (1080) (see FIG. 9). With shaft assembly (1414) positioned at the center of base (1376), shaft assembly (1414) is coaxial with ultrasonic surgical instrument driver axis (74) when attached. Thus, rotation of rotational assembly (70) is configured to cause shaft assembly (1414) of ultrasonic surgical instrument (1314) to rotate about its own longitudinal axis. In other words, it should be understood that ultrasonic surgical instrument (1414) is configured to be rotated by rotational assembly (70) of robotic arm (32) such that individual components of ultrasonic surgical instrument (1314) (e.g., shaft assembly (1414)) do not need to rotate independently of other portions of ultrasonic surgical instrument (1314).

As also with ultrasonic surgical instrument (14), ultrasonic surgical instrument (1314) of the present example includes the instrument-based insertion architecture described above. To this end, shaft assembly (1414) includes an end effector (not shown) on a distal end thereof that is substantially similar to end effector (1116) described above. To facilitate such instrument-based insertion, insertion of shaft assembly (1414) is grounded at instrument base (1376) such that the end effector is configured to selectively move longitudinally from a retracted position to an extended position, vice versa, and any desired longitudinal position therebetween. As used herein, the retracted position places the end effector relatively close and proximally toward instrument base (1376), whereas the extended position places the end effector relatively far and distally away from instrument base (1376). Insertion into and withdrawal of the end effector relative to the patient may thus be facilitated by ultrasonic surgical instrument (1314), although it will be appreciated that such insertion into and withdrawal may also occur via robotic arms (32) in one or more examples.

As with ultrasonic surgical instrument (1014) described above, ultrasonic surgical instrument (1314) of the present example includes various drive components configured to move shaft assembly (1414) between the retracted position and the extended position. For instance, the interior of ultrasonic surgical instrument (1314) includes a carrier (1500) having one or more guide rails (1510), a translation driver (1512), an actuation driver (1518) and a carriage (1520). As similarly described above, guide rails (1510) extend axially between proximal end portion (1506) and a distal end portion (not shown) and in some contexts may be supported by an outer housing of ultrasonic surgical instrument (1314). As will be discussed in greater detail below, guide rails (1510) are generally configured to guide or otherwise direct movement of carriage (1520) along a predetermined axial path.

Translation driver (1512) and actuation driver (1518) are substantially similar to translation driver (1212) and actuation driver (1218) described above. For instance, like translation driver (1212), translation driver (1512) of the present example is generally configured to drive translation of carriage (1520) by rotation of translation driver (1512) using drive output (68) of robotic arm (32). Similarly, actuation driver (1518) is generally configured to selectively drive various portions of ultrasonic surgical instrument (1314) from one or more drive outputs (68) of robotic arm (32). As noted above, in merely one example, actuation driver (1518) is configured to drive actuation of the end effector between an open position and a closed position using various drive components such as gears, cams, links, cranks, lead screws, and/or etc.

Carriage (1520) of the present example is likewise substantially similar to carriage (1220) described above. For instance, like with carriage (1220), carriage (1520) of the present example is positioned between guide rails (1510) such that carriage (1520) is generally configured to move axially along guide rails (1510) under the influence of translation driver (1512). Additionally, carriage (1520) includes a distal guide (1522), a proximal guide (1526), and a transducer housing (1530) extending distally from proximal guide (1526). Both distal guide (1522) and proximal guide (1526) include a plurality of guide slots (1524, 1528) configured to receive guide rails (1510). Thus, distal guide (1522) and proximal guide (1526) are both configured to confine movement of carriage (1520) along the path defined by guide rails (1510) via guide slots (1524, 1528).

As similarly described above with respect to transducer housing (1230), transducer housing (1530) of the present example is configured to receive a transducer assembly (1454). Transducer housing (1530) is substantially similar to transducer housing (1230) described above in that transducer housing (1530) (and/or proximal end portion (1506)) of the present example may be configured to fixedly secure transducer assembly (1454), thereby acting as a mechanical ground to stabilize transducer assembly (1454) and other components of the acoustic drivetrain.

Transducer assembly (1454) of the present example is substantially similar to transducer assembly (1154) described above. For instance, transducer assembly (1454) of the present example may be connected to a generator (not shown) similar to generator (155) of the acoustic drivetrain. Thus, the generator can be used to apply electric power to transducer assembly (1454) to activate piezoelectric elements (not shown) in transducer assembly (1454) and thereby convert the electrical power into ultrasonic vibrations. As with transducer assembly (1154) described above, transducer assembly (1454) of the present example includes a transducer body (1460) housing the piezoelectric elements, an attachment flange (not shown), and a horn (1468).

Although not shown, it should be understood that the attachment flange of transducer assembly (1454) may be readily used to ground transducer assembly (1454) relative to transducer housing (1530). As such, the attachment flange of transducer assembly (1454) extends outwardly from transducer body (1460) defining a generally circular shape interrupted by one or more engagement portions or flats (not shown). As similarly described above with respect to attachment flange (1162), such features of the attachment flange in the present example may be generally configured to engage portions of transducer housing (1530) and/or proximal guide (1526) to fixedly secure transducer assembly (1454) to carriage (1520).

Figure 17:
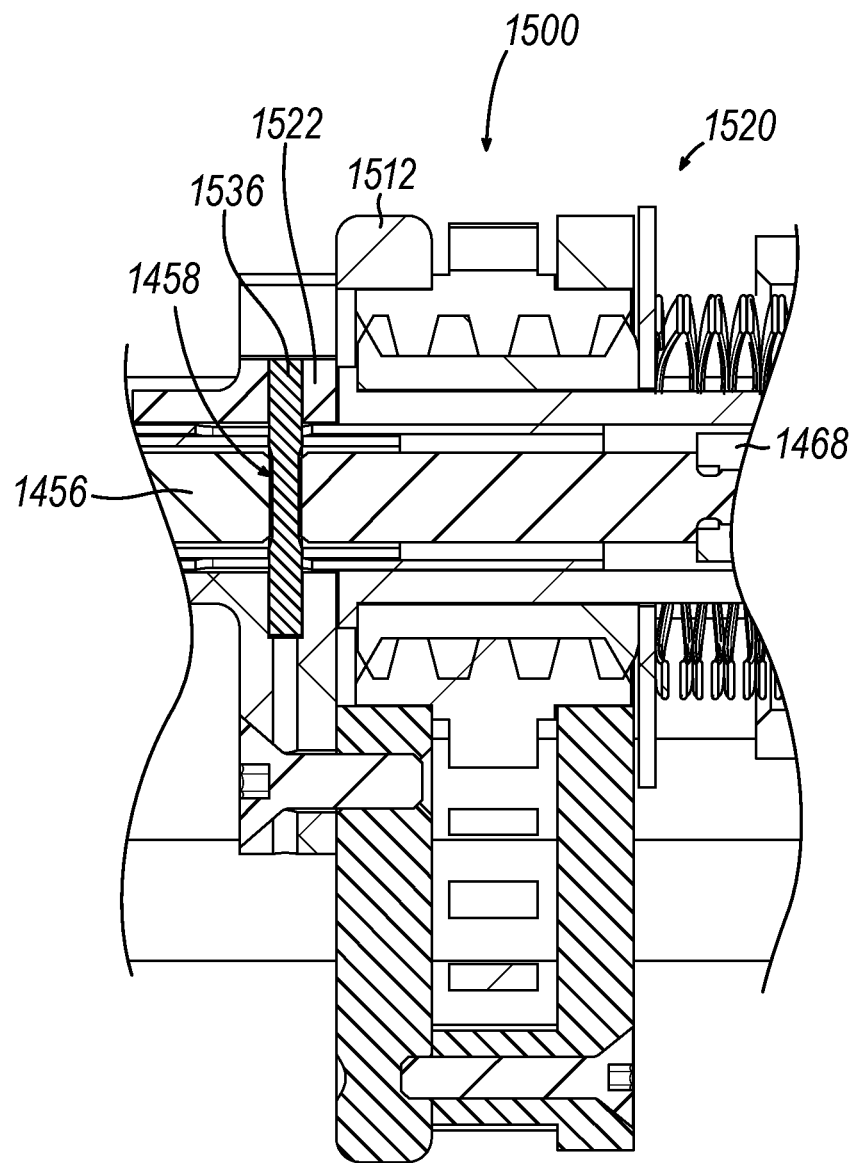
FIG. 17 depicts a cross-sectional view of the surgical instrument of FIG. 16, the cross-section taken along section line 17-17 of FIG. 16.

As with transducer assembly (1154) discussed above, transducer assembly (1454) of the present example is a part of the acoustic drivetrain, which also includes an acoustic waveguide (1456) (see FIG. 17). Transducer assembly (1454) and acoustic waveguide (1456) are together used to transmit ultrasonic energy from transducer assembly (1454) to the blade of shaft assembly (1414) to thereby cut tissue.

Acoustic waveguide (1456) (see FIG. 17) of the present example is substantially similar to acoustic waveguide (1156) discussed above. However, as best seen in FIG. 17, unlike acoustic waveguide (1156) discussed above, acoustic waveguide (1456) of the present example includes a ground bore (1458) proximate the proximal end of acoustic waveguide (1456). Ground bore (1458) is configured to receive a ground pin (1536) that can be used to provide additional stability to acoustic waveguide (1456) and/or the blade. In some examples, the particular position of ground bore (1458) may correspond to the position of an acoustic node along the length of acoustic waveguide (1456).

As noted above and referring back to FIG. 16 in conjunction with FIG. 17, transducer assembly (1454) may be grounded relative to transducer housing (1530) by fixedly securing transducer assembly (1454) within transducer housing (1530) using the flange of transducer assembly (1454) or other fixation means. Such a configuration can generally be desirable to provide stability to the acoustic drivetrain and/or blade. However, in some contexts, additional stability may be desired than can be achieved using fixation of transducer assembly (1454) alone. By way of example only, such additional stability may be desirable where acoustic waveguide (1456) has a particularly long length. In such contexts, acoustic waveguide (1456) may be configured as shown with ground bore (1458). With such a ground bore (1458), ground pin (1536) extends through acoustic waveguide (1456) and into distal guide (1522), which may include or one or more brackets fixedly secure acoustic waveguide (1456) relative to carriage (1520). Such a configuration can be used in addition to fixation via transducer assembly (1454) to provide additional stability to the acoustic drivetrain.

III. Exemplary Alternative Shaft Assembly for Ultrasonic Surgical Instrument

As noted above, an acoustic waveguide similar to acoustic waveguides (156, 1156, 1456) may use structures configured to acoustically isolate the acoustic waveguide from other adjacent structures. In some examples, such structures can be configured as material overmolded to the surface of the acoustic waveguide, such as isolation structure (1159) discussed above. However, the process of applying one or more overmolds to the surface of the acoustic waveguide can include high manufacturing costs. In addition, supply chain challenges may lead to increased lead time. Thus, in some examples, it may be desirable to configure the acoustic waveguide for acoustical isolation from other adjacent components without the need for overmolded parts. Although various suitable acoustic waveguides and associated components are described herein in specific configurations and in combination with specific components, it should be understood that in other examples, such acoustic waveguides may be arranged in other suitable configurations and with other components.

Figure 18:
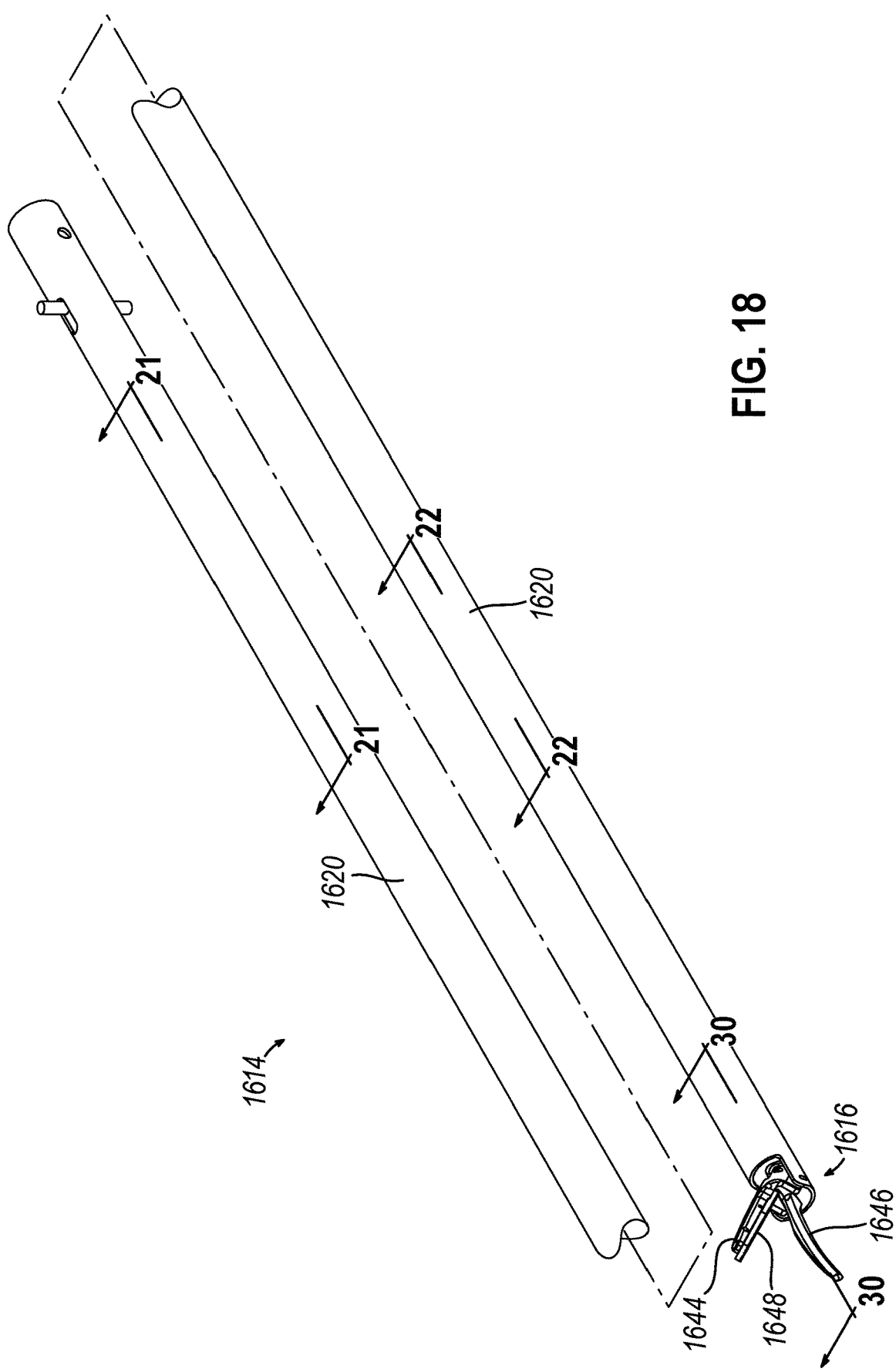
FIG. 18 depicts a perspective view of an exemplary alternative shaft assembly for use with any one of the surgical instruments of FIG. 6A, 9 or 16.

FIG. 18 shows an exemplary alternative shaft assembly (1614) that can be readily used with any one of ultrasonic surgical instruments (14, 1014, 1314) described above. As can be seen, shaft assembly (1614) comprises an outer tube (1620) and an inner tube (1622) (see FIG. 21) extending the length of shaft assembly (1614) with an end effector (1616) on a distal end thereof. End effector (1616) is substantially similar to end effectors (116, 1116) described above. For instance, end effector (1616) includes a clamp arm (1644) having a clamp pad (1648) and a blade (1646). Clamp arm (1644) is generally pivotable relative to blade (1646) to clamp tissue between clamp pad (1648) and blade (1646). Blade (1646) may then be used to sever and/or seal tissue clamped therebetween.

Figure 19:
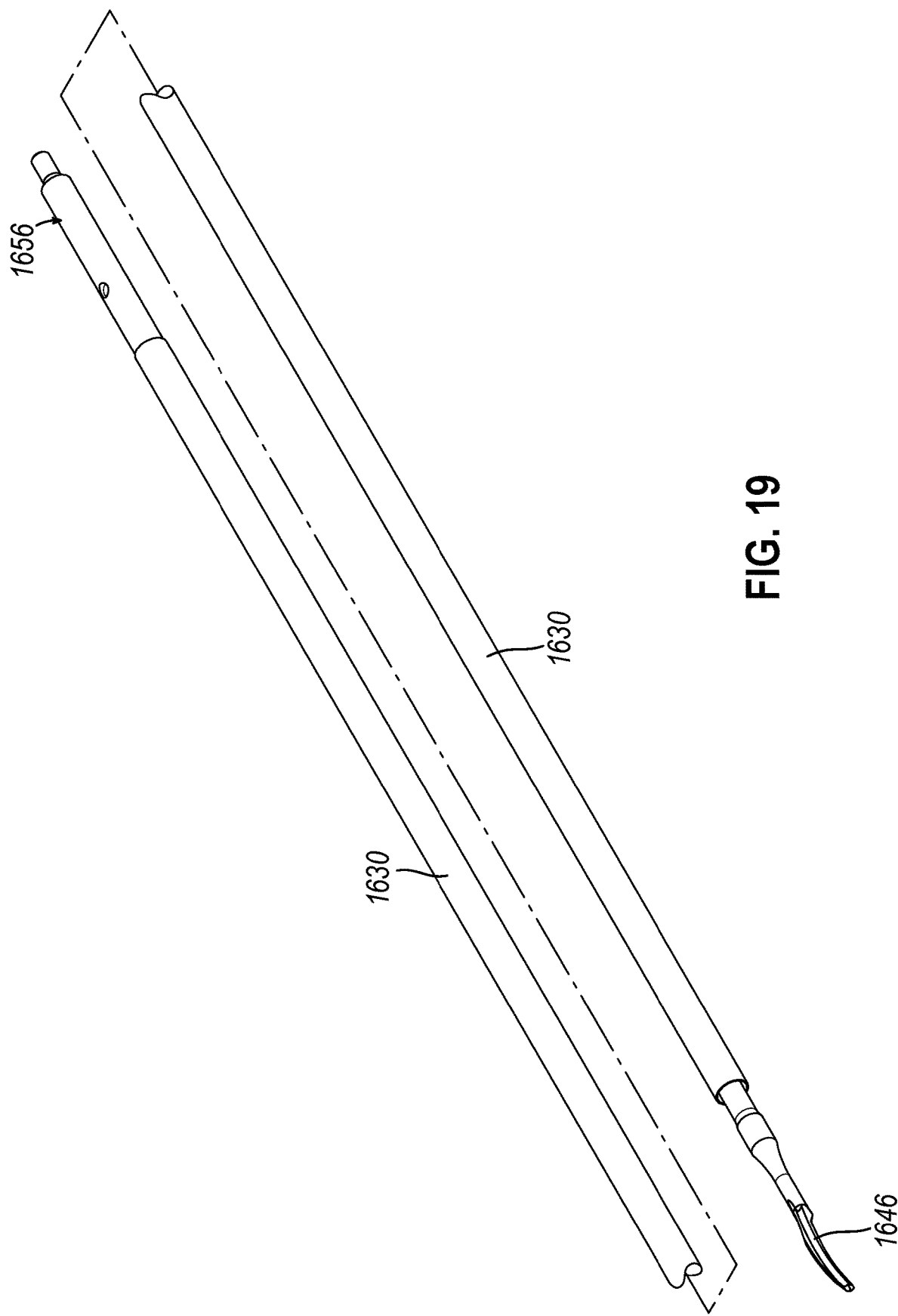
FIG. 19 depicts another perspective view of the shaft assembly of FIG. 18, with an outer tube and an inner tube removed.

As best seen in FIG. 19, shaft assembly (1614) (see FIG. 18) further includes a sheath (1630) projecting proximally relative to blade (1646) within outer and inner tubes (1620, 1622). Sheath (1630) is shaped as an elongate hollow cylindrical structure extending for nearly the entire length of shaft assembly (1614) (see FIG. 21). As will be described in greater detail below, sheath (1630) is generally configured to isolate an acoustic waveguide (1656) of shaft assembly (1614) (see FIG. 21) from other components such as outer and inner tubes (1620, 1622) (see FIG. 21). As such, it should be understood that sheath (1630) can comprise a variety of acoustically isolating materials such as polymers, silicon, natural and/or synthetic rubbers, wood, and/or etc.

Figure 20:
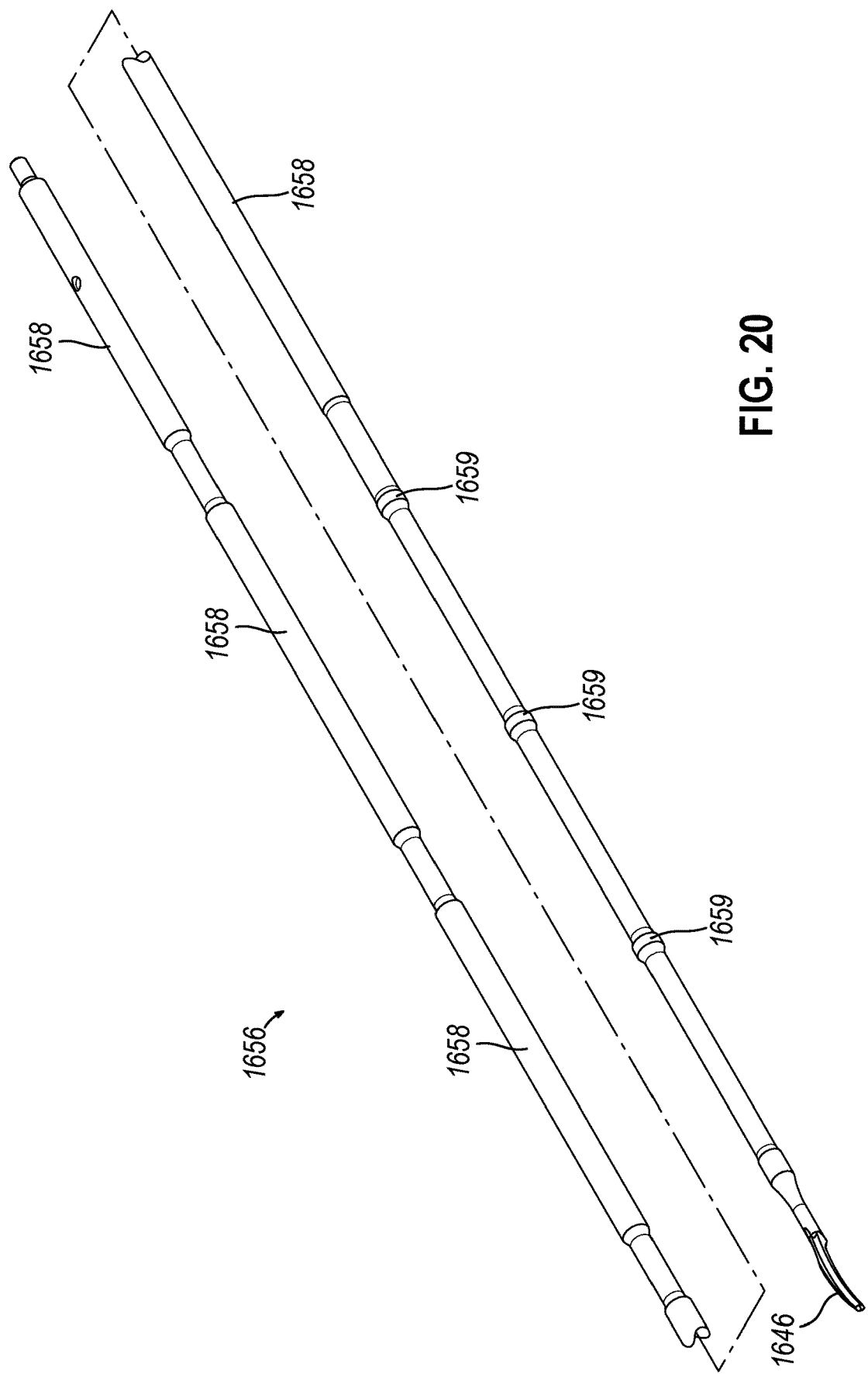
FIG. 20 depicts a perspective view of an acoustic waveguide of the shaft assembly of FIG. 18.

As best seen in FIG. 20, shaft assembly (1614) (see FIG. 18) further includes an acoustic waveguide (1656) extending proximally from blade (1646) such that acoustic waveguide (1656) and blade (1646) are of integral construction. Although blade (1646) and acoustic waveguide (1656) are of integral construction in the present example, it should be understood that in other examples, blade (1646) can be a separate discrete component from acoustic waveguide (1656) fixedly secured thereto.

As with acoustic waveguides (156, 1156, 1456) discussed above, acoustic waveguide (1656) is configured to be a part of an acoustic drivetrain that directs ultrasonic energy from a transducer assembly (not shown) to blade (1646). As such, acoustic waveguide (1656) includes one or more damping structures (1658) and one or more isolation structures (1659) configured to manage vibrations as ultrasonic energy is transferred to blade (1646) through acoustic waveguide (1656). For instance, acoustic waveguide (1656) includes a plurality of damping structures (1658) oriented towards the proximal end of acoustic waveguide (1656). Damping structures (1658) are generally defined by relatively thick (or increased cylindrical diameter) elongate sections of acoustic waveguide (1656). Each damping structure (1658) is positioned adjacent to an acoustical node of acoustic waveguide (1656) such that the length of each damping structure (1658) generally extends between two acoustical nodes. This positioning and the general thickness or diameter of each dampening structure (1658) is generally configured to provide damping of undesirable transverse vibrations during use of acoustic waveguide (1656).

Acoustic waveguide (1656) further defines a plurality of isolation structures (1659) oriented towards the distal end of acoustic waveguide (1656). Isolation structures (1659) are generally configured to acoustically isolate acoustic waveguide (1656) and/or blade (1646) from other portions of shaft assembly (1614). Each isolation structure (1659) is positioned at an acoustical node of acoustic waveguide (1656) to reduce interference with ultrasonic energy being transmitted through acoustic waveguide (1656). In the present example, each isolation structure (1659) is defined by an outward cylindrical projection or flange extending from the outer surface of acoustic waveguide (1656). In other words, each isolation structure (1659) is defined by acoustic waveguide (1656) itself such that each isolation structure (1659) is integral with acoustic waveguide (1656). Thus, it should be understood that isolation structures (1659) of the present example comprise the same material as acoustic waveguide (1656). Although isolation structures (1659) of the present example are shown as being associated with acoustic waveguide (1656), it should be understood that in other examples, one or more isolation structures (1659) may also be defined by blade (1646).

Figure 23:
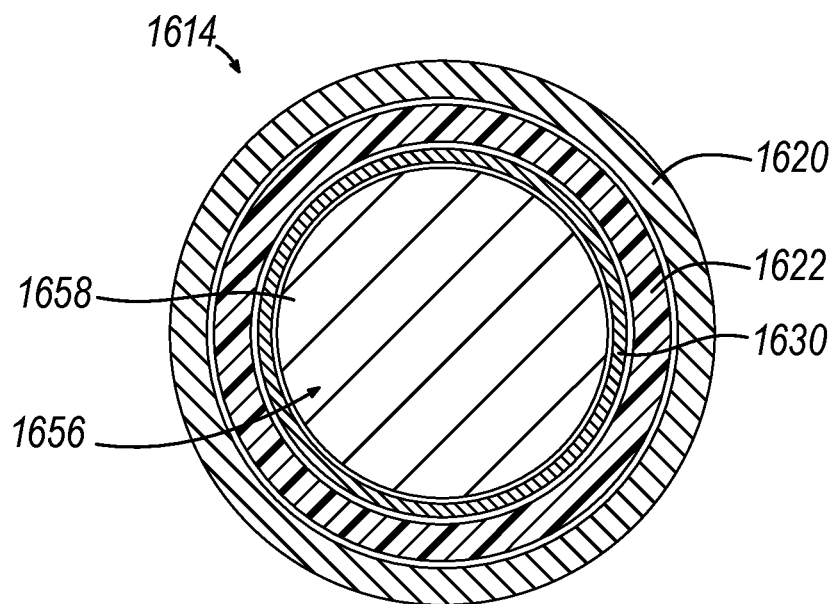
FIG. 23 depicts yet another cross-sectional view of the shaft assembly of FIG. 18, the cross-section taken along section line 23-23 of FIG. 21.

As can be seen in FIGS. 21 and 23, sheath (1630) is configured with an inner diameter that is approximately equivalent to the outer diameter of each damping structure (1658). This configuration provides an engineered fit between sheath (1630) and each damping structure (1658). Because sheath (1630) comprises an acoustically insulative material, this engineered fit substantially reduces the propagation of transverse vibrations through sheath (1630) to other components of shaft assembly (1614) such as outer and inner tubes (1620, 1622).

As can be seen in FIG. 22, the inner diameter of sheath (1630) is also configured to corresponding to the outer diameter of each isolation structure (1659). As similarly described above with respect to damping structure (1658), this configuration likewise provides an engineered fit between sheath (1630) and each isolation structure (1659). As similarly noted above, this engineered fit along with sheath (1630) comprising an acoustically insulative material substantially reduces the propagation of vibrations through sheath (1630). Accordingly, sheath (1630) and isolation structures (1659) operate to cooperatively isolate acoustic waveguide (1656) from other structures of shaft assembly (1614) such as outer and inner tubes (1620, 1622).

Additionally, since isolation structures (1659) are oriented towards the distal end of acoustic waveguide (1656), it should be understood that in some contexts, the engagement between sheath (1630) and isolation structures (1659) can provide a sealing feature. This sealing feature may provide the functionality of fluidly isolating the interior of shaft assembly (1614) from the exterior of shaft assembly (1614). Accordingly, sheath (1630) and isolation structures (1659) also operate to cooperatively prevent ingress of fluid into outer and inner tubes (1620, 1622), prevent ingress of fluid against acoustic waveguide (1656), and/or inhibit damage to nearby components.

Figure 24:
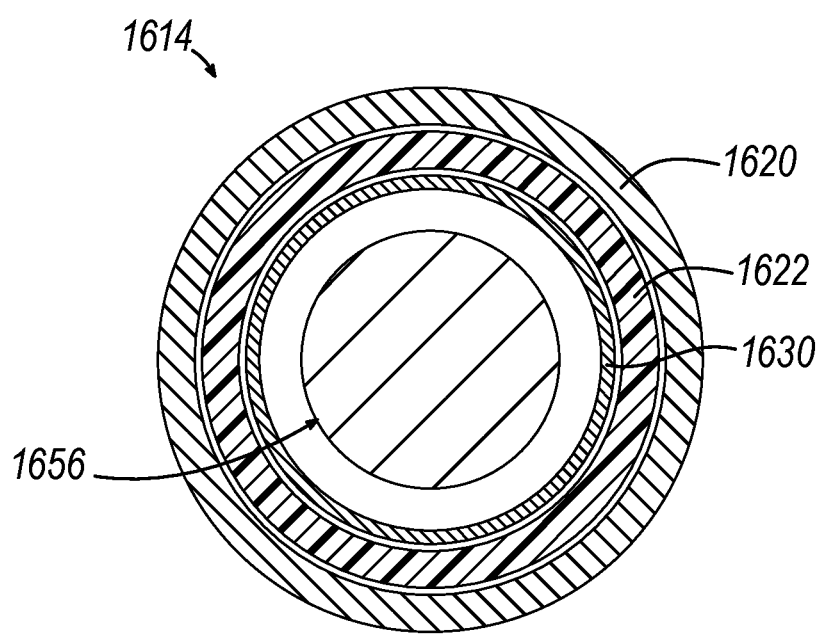
FIG. 24 depicts still another cross-sectional view of the shaft assembly of FIG. 18, the cross-section taken along section line 24-24 of FIG. 21.

It should be understood that sheath (1630) of the present example has a generally consistent inner diameter along the length of sheath (1630). For instance, as best seen in FIGS. 21, 22, and 24, sheath (1630) remains consistent in diameter even when acoustic waveguide (1656) decreases in diameter, tapers, or necks at the spaces between damping structures (1658) and isolation structures (1659). As such, a gap is generally formed between sheath (1630) and acoustic waveguide (1656) between each damping structure (1658) and between each isolation structure (1659). It should be understood that such a gap is merely optional and may be reduced or even omitted in some examples. For instance, in some examples sheath (1630) may be flexible and may further define an interference fit with acoustic waveguide (1656). Thus, sheath (1630) may flex in some examples to fill or reduce gaps where acoustic waveguide (1656) reduces in thickness. In other examples, the inner dimeter of sheath (1630) may vary along the length of sheath (1630) to account for changes in the diameter of acoustic waveguide (1656). In such examples, this changing inner diameter of sheath (1630) may reduce or even eliminate such gaps entirely.

Figure 25:
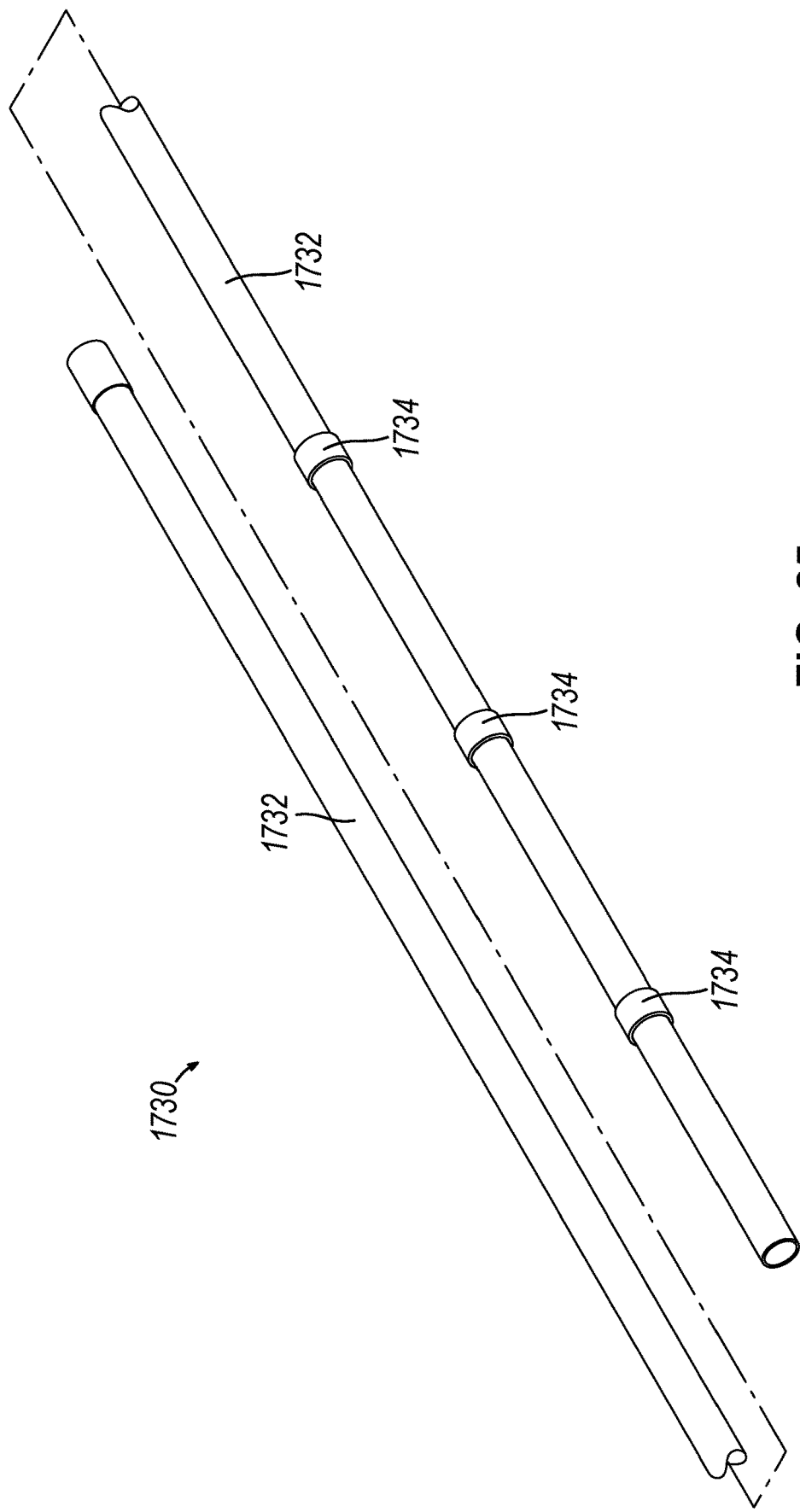
FIG. 25 depicts a perspective view of an exemplary alternative sheath assembly for use with the shaft assembly of FIG. 18.
Figure 26:
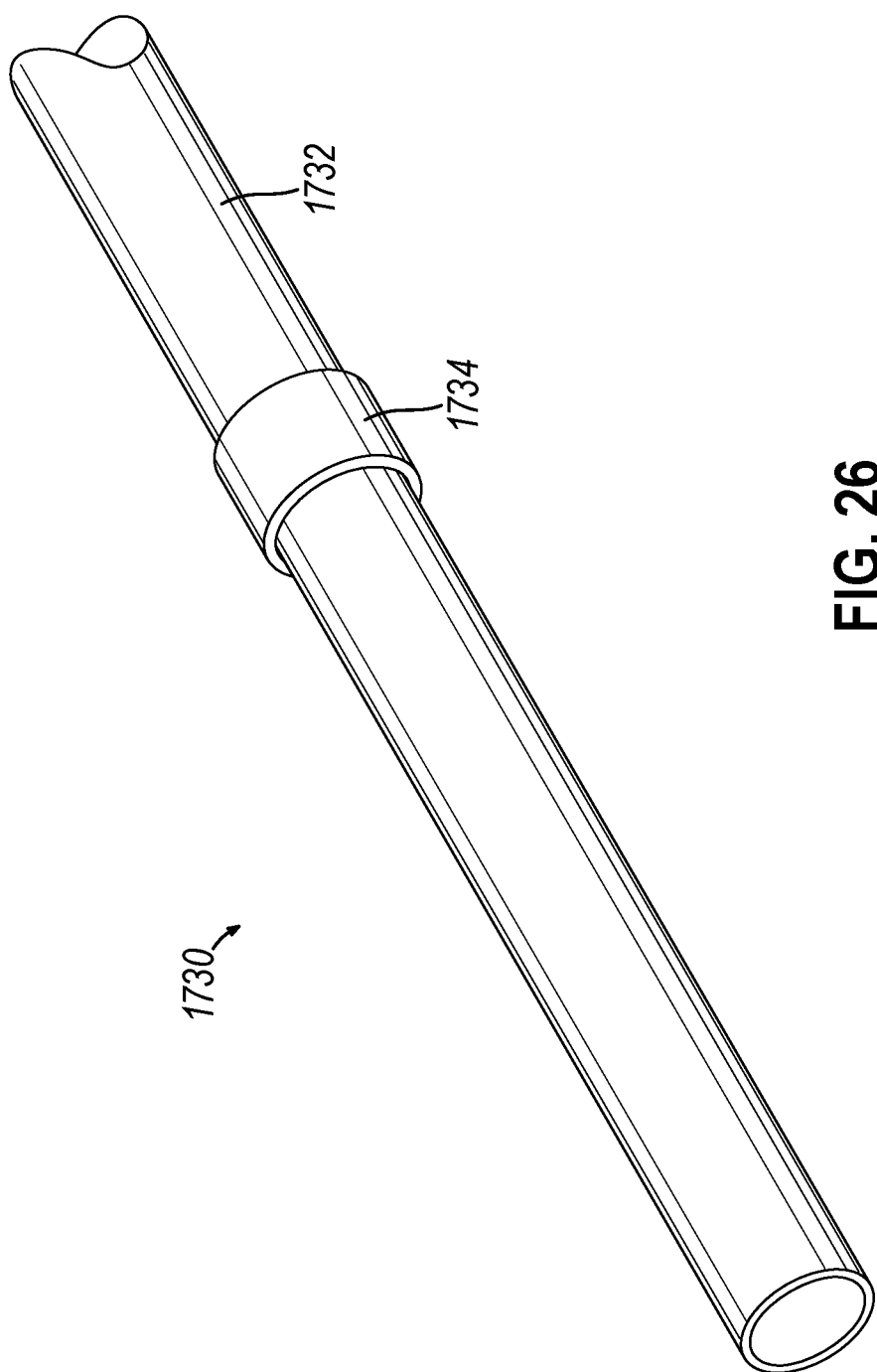
FIG. 26 depicts a detailed perspective view of the sheath assembly of FIG. 25.

IV. Exemplary Alternative Sheath Assemblies for Use with Shaft Assembly of Ultrasonic Surgical Instrument FIGS. 25 and 26 show an exemplary alternative sheath assembly (1730) that may be readily used with shaft assembly (1614) (see FIG. 27) described above in lieu of sheath (1630). As can be seen, sheath assembly (1730) comprises an elongate tubular sheath (1732) and a plurality of damping rings (1734) spaced along the outer surface of sheath (1732). Sheath (1732) is substantially similar to sheath (1630) described above. For instance, as with sheath (1630), sheath (1732) of the present example is shaped as an elongate hollow cylindrical structure extending for nearly the entire length of shaft assembly (1614) (see FIG. 27). As will be described in greater detail below and with respect to FIG. 27, sheath (1732) is generally configured to isolate acoustic waveguide (1656) of shaft assembly (1614) from other components such as outer and inner tubes (1620, 1622). As such, it should be understood that sheath (1732) can comprise a variety of acoustically isolating materials such as polymers, silicon, natural and/or synthetic rubbers, wood, and/or etc.

Figure 27:
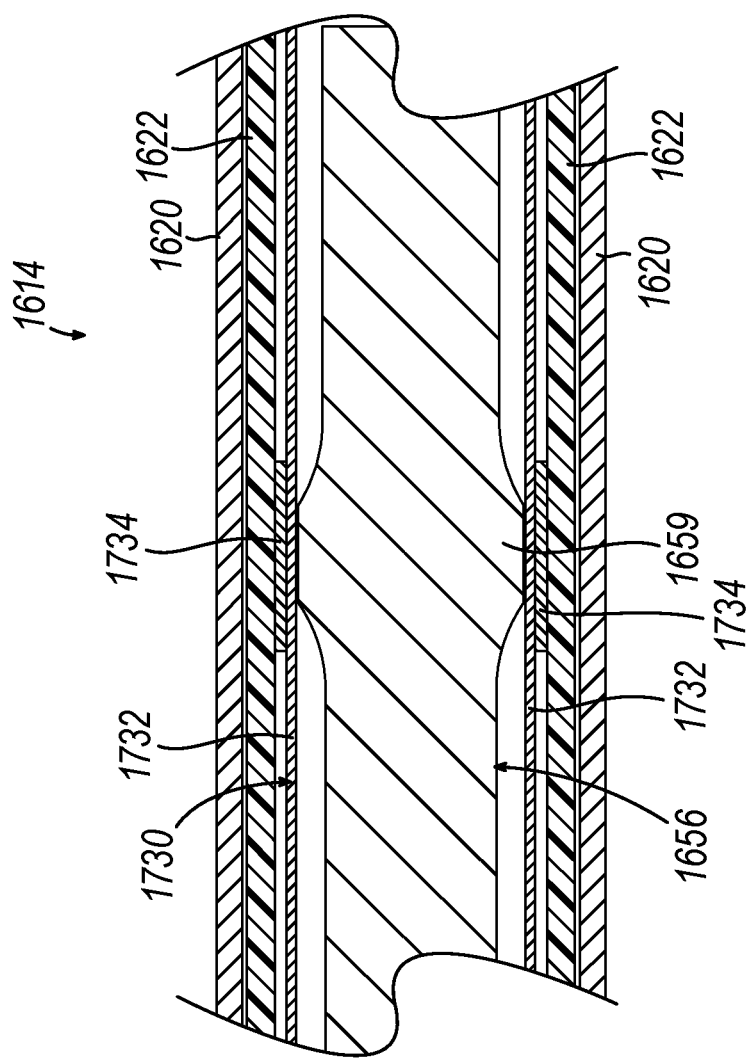
FIG. 27 depicts a cross-sectional view of the shaft assembly of FIG. 18 with the sheath assembly of FIG. 25 integrated therewith.

As shown in FIGS. 25 and 27, damping rings (1734) are disposed on the outer surface of sheath (1732) at various positions along the axial length of sheath (1732). The particular position of damping rings (1734) generally correspond to the position of each isolation structure (1659) of acoustic waveguide (1656) described above. Sheath assembly (1730) of the present example is shown as having three damping rings (1734). However, in other examples, various suitable alternative number of damping rings (1734) may be used. For instance, here the particular number of damping rings (1734) corresponds to the particular number of isolation structures (1659) defined by acoustic waveguide (1656). Thus, in examples with more or less isolation structures (1659) are used, more or less damping rings (1734) may respectively be used.

Each damping ring (1734) in the present example comprises a hollow cylindrical member formed of silicon or silicon-like material. The particular structure and/or material of each damping ring (1734) permits each damping ring (1734) to act as a well damped acoustic ground relative to other portions of shaft assembly (1614) such as outer or inner tubes (1620, 1622). Although the present material for each damping ring (1734) includes silicon or a silicon-like material, it should be understood that in other examples, various alternative acoustically insulative materials may be used. By way of example only, suitable acoustically insulative materials can include polymers, natural and/or synthetic rubbers, wood, and/or etc.

In the present example, each damping ring (1734) is bonded or fixedly secured to the exterior of sheath (1732). Such bonding may be accomplished by a variety of mechanisms. For instance, in the present example, bonding is accomplished by overmolding each damping ring (1734) to the outer surface of sheath (1732). In other examples, each damping ring (1734) can alternatively be bonded using an adhesive bond or by welding (e.g., ultrasonic welding). In yet other examples, each damping ring (1734) can be fixedly secured to the surface of sheath (1732) by a press or compression fit. In still other examples, each damping ring (1734) may instead be integral with sheath (1732) such that the structure of each damping ring (1734) is molded, 3-D printed, or cut into the outer surface of sheath (1732). Still other alternative means of bonding or otherwise forming the structure of each damping ring (1734) on the outer surface of sheath (1732) will be apparent to those of ordinary skill in the art in view of the teachings herein.

FIG. 27 shows the relationship between sheath assembly (1730) and shaft assembly (1614) when sheath assembly (1730) is used in lieu of sheath (1630) discussed above. As can be seen, sheath (1732) is disposed adjacent to acoustic waveguide (1656), similar to the position of sheath (1630) described above. However, each damping ring (1734) is positioned between sheath (1732) and inner tube (1622) of shaft assembly (1614). Additionally, as noted above, each damping ring (1734) is positioned on sheath (1732) to correspond to the position of a corresponding isolation structure (1659) of acoustic waveguide (1656). As such, each damping ring (1734) is configured to prevent the propagation of ultrasonic vibrations from acoustic waveguide (1656) to other portions of shaft assembly (1614) such as outer and inner tubes (1620, 1622).

Figure 28:
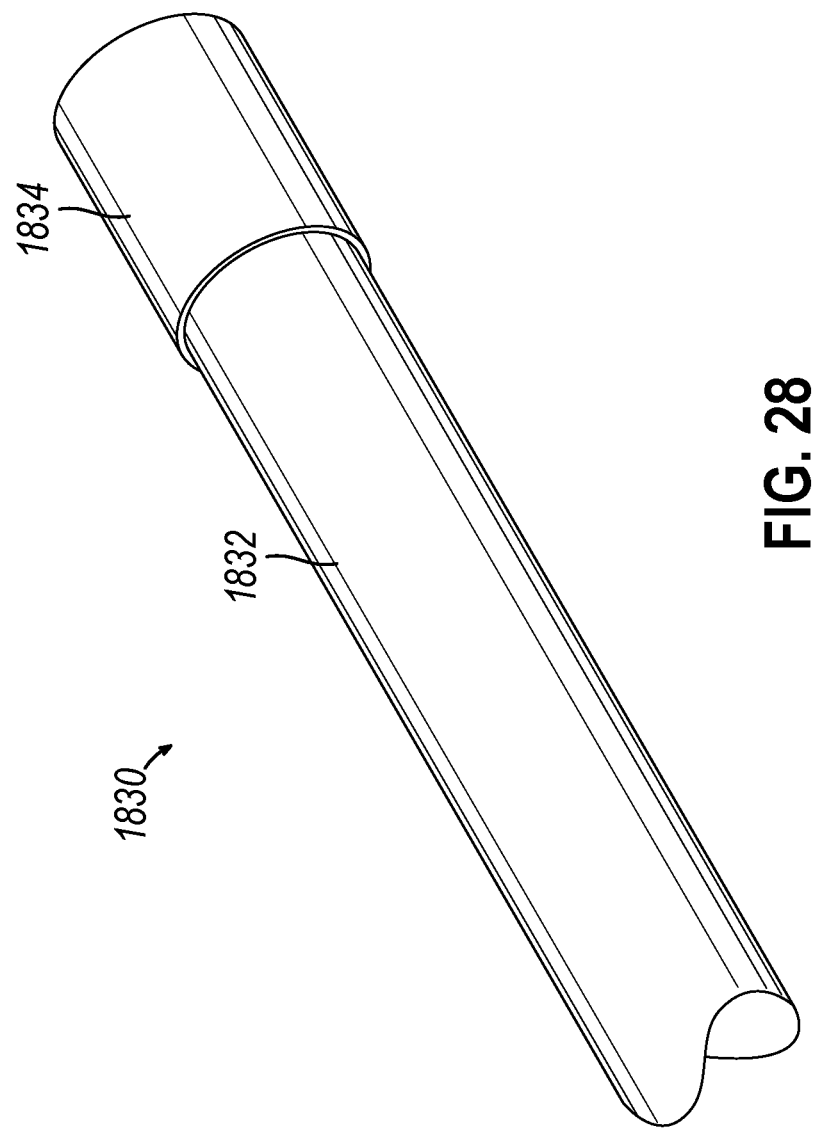
FIG. 28 depicts a perspective view of another exemplary alternative sheath assembly for use with the shaft assembly of FIG. 18.
Figure 29:
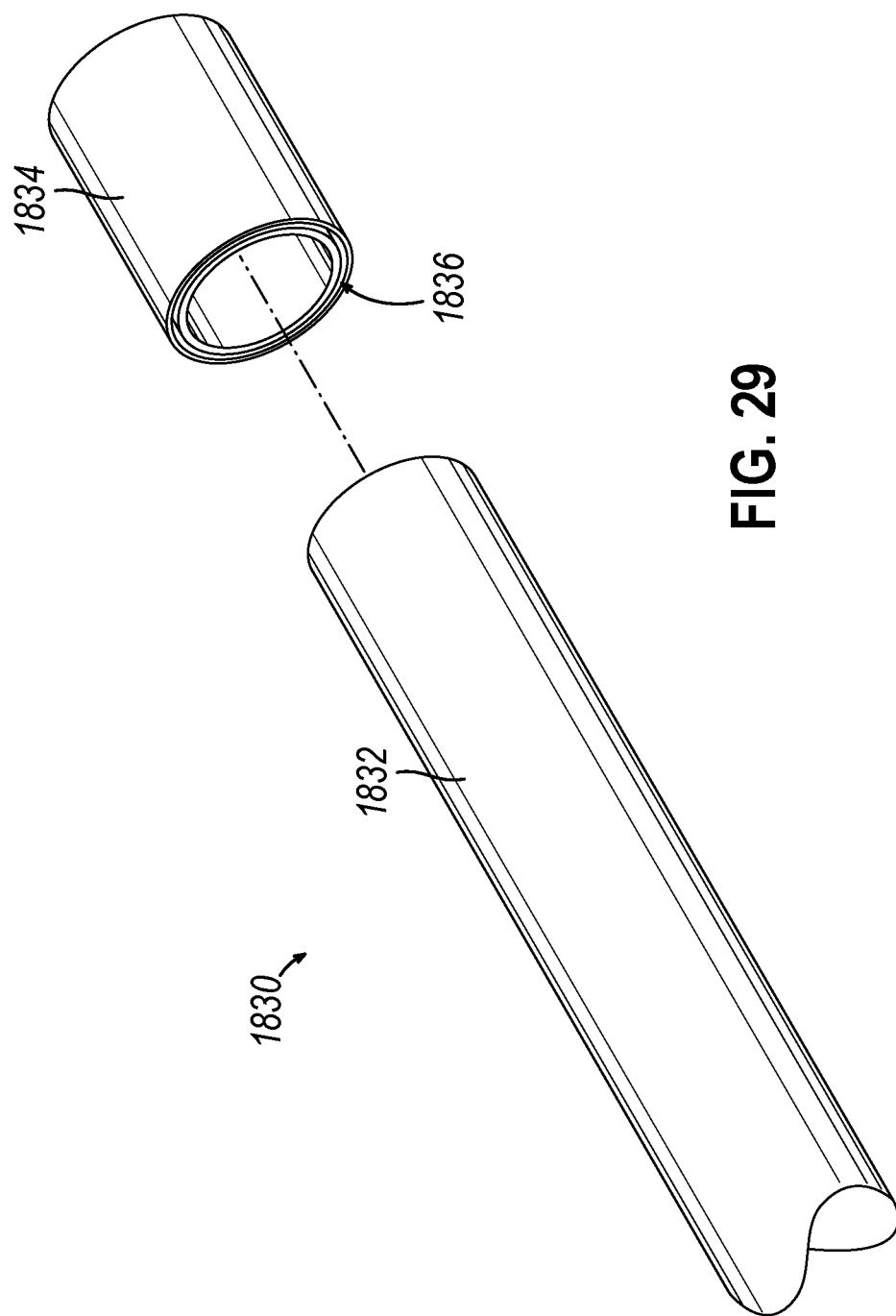
FIG. 29 depicts an exploded perspective view of the sheath assembly of FIG. 28.
Figure 30:
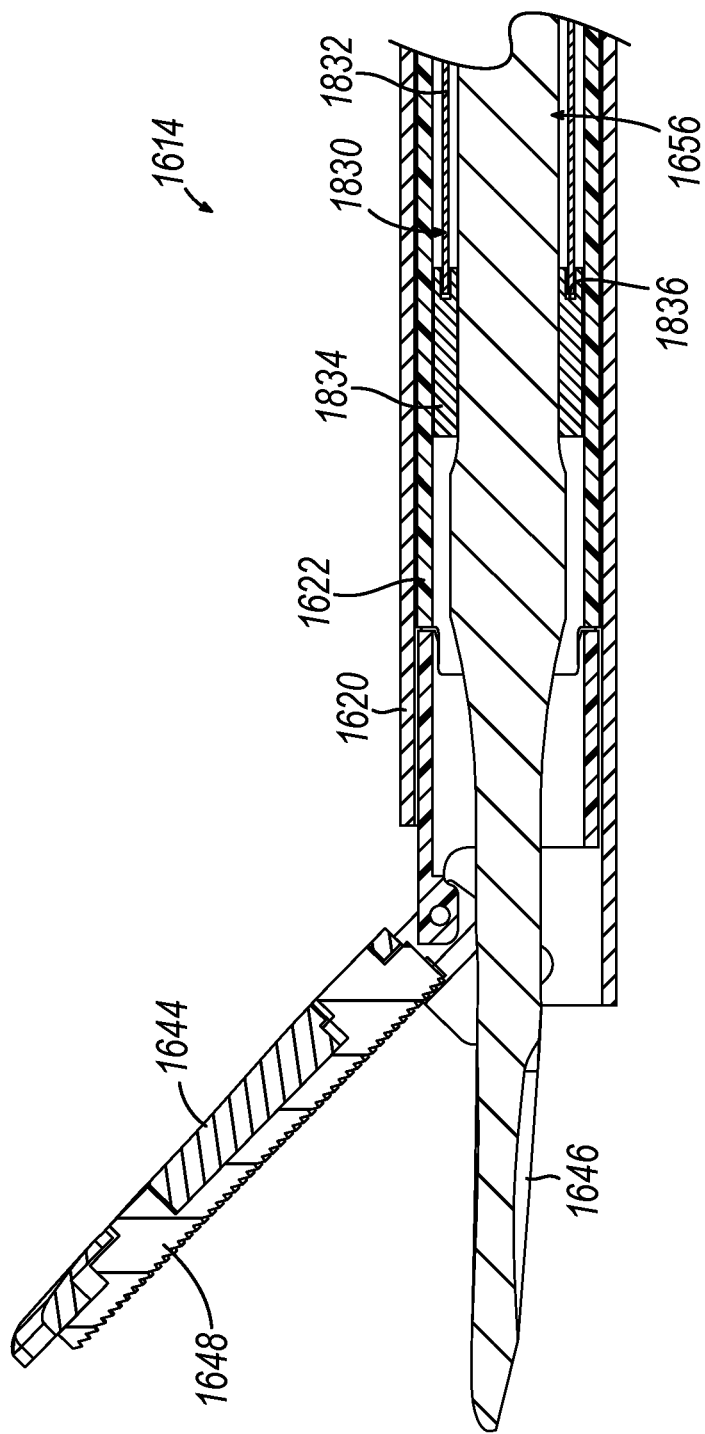
FIG. 30 depicts a cross-sectional view of the shaft assembly of FIG. 18 with the sheath assembly of FIG. 28 integrated therewith.

FIGS. 28-30 show another exemplary alternative sheath assembly (1830) that may be readily used with shaft assembly (1614) described above in lieu of sheath (1630) or sheath assembly (1730). As can be seen, sheath assembly (1830) comprises an elongate tubular sheath (1832) and a sheath cap (1834) disposed on a distal end of sheath (1832). Sheath (1832) is substantially similar to sheaths (1630, 1732) described above. For instance, as with sheath (1630), sheath (1832) of the present example is shaped as an elongate hollow cylindrical structure extending for nearly the entire length of shaft assembly (1614). As will be described in greater detail below, sheath (1832) is generally configured to isolate acoustic waveguide (1656) of shaft assembly (1614) from other components such as outer and inner tubes (1620, 1622). As such, it should be understood that sheath (1832) can comprise a variety of acoustically isolating materials such as polymers, silicon, natural and/or synthetic rubbers, wood, and/or etc.

Sheath cap (1834) is disposed on the distal end of sheath (1832) and is generally configured to seal the distal end of sheath (1832) to thereby prevent fluid ingress into sheath (1832) and or other components of shaft assembly (1614) such as outer or inner tubes (1620, 1622). As best seen in FIG. 29, sheath cap (1834) includes a receiving channel (1836) configured to receive at least a portion of the distal end of sheath (1832). As will be described in greater detail below, sheath cap (1834) may also be configured to damp ultrasonic vibrations from acoustic waveguide (1656) (see FIG. 30) and/or blade (1646) (see FIG. 30). As such, sheath cap (1834) may comprise an acoustically insulative material such as silicon or a silicon-like material. By way of example only, other suitable materials for sheath cap (1834) may include polymers, natural and/or synthetic rubbers, wood, and/or etc.

Sheath cap (1834) is generally fixedly secured or fastened to the distal end of sheath (1832). By way of example only, in some examples, sheath cap (1834) is overmolded onto sheath (1834). In other examples, sheath cap (1834) may alternatively be bonded using an adhesive bond or by welding (e.g., ultrasonic welding). In yet other examples, sheath cap (1834) can be fixedly secured to the distal end of sheath (1832) by a press or compression fit. In still other examples, sheath cap (1834) may instead be integral with sheath (1832) such that the structure of sheath cap (1834) is molded, 3-D printed, or cut into the distal end of sheath (1832). Still other alternative means of bonding or otherwise forming the structure of each damping ring (1734) on the outer surface of sheath (1732) will be apparent to those of ordinary skill in the art in view of the teachings herein.

FIG. 30 shows the relationship between sheath assembly (1830) and shaft assembly (1614) when sheath assembly (1830) is used in lieu of sheath (1630) discussed above. As can be seen, sheath (1832) is disposed adjacent to acoustic waveguide (1656), similar to the position of sheath (1630) described above. However, unlike sheath (1630) described above, sheath (1832) of the present example includes sheath cap (1834) disposed at the distal end of sheath (1832). Sheath cap (1834) is positioned in the space between acoustic waveguide (1656) and inner tube (1622). As such, sheath cap (1834) is configured to provide a fluid seal to prevent the proximal ingress of fluid into inner tube (1622) and/or sheath (1832). Additionally, as noted above, sheath cap (1834) may have acoustically insulative properties. Thus, sheath cap (1834) may be further configured to prevent the propagation of acoustic vibrations from acoustic waveguide (1656) and/or blade (1646) to other structures of shaft assembly (1614) such as inner and outer tubes (1620, 1622).

Although not shown, it should be understood that in other examples, sheath cap (1834) may be readily used with various other sheaths. For instance, in some examples, sheath cap (1834) can be used in combination with sheath (1630) described above to obtain the benefits of sheath cap (1834) and the damping provided by sheath (1630). Alternatively, in other examples, sheath cap (1834) may be used with sheath (1732) and/or damping rings (1734) described above to obtain the benefits of sheath cap (1834) and the damping provided by the combination of sheath (1732) and damping rings (1734). Of course, various other combinations of sheath cap (1834) with other elements may be used as will be apparent to those of ordinary skill in the art in view of the teachings herein.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: an end effector including an ultrasonic blade; an ultrasonic transducer assembly; and a shaft assembly, including: a tube, an acoustic waveguide received within the tube and acoustically connected between the ultrasonic blade and ultrasonic transducer assembly to communicate ultrasonic vibrations from the ultrasonic transducer assembly to the ultrasonic blade, wherein the acoustic waveguide extends along a longitudinal axis, and a sheath radially positioned between the acoustic waveguide and the tube and including: a sheath body having an outer body surface, and a plurality of damping rings radially extending from the outer body surface and engaged with the tube, wherein the plurality of damping rings are configured to acoustically isolate the acoustic waveguide from the tube.

Example 2

The ultrasonic surgical instrument of Example 1, wherein the acoustic waveguide further includes: an acoustic body extending along the longitudinal axis and defining a body radial diameter about the longitudinal axis, a first isolation structure radially extending about the acoustic body a first radial diameter, wherein the first radial diameter is larger than the body radial diameter, and a second isolation structure radially extending about the acoustic body a second radial diameter and longitudinally spaced from the first isolation structure, wherein the first second radial diameter are larger than the body radial diameter, wherein the first and the second isolation structures respectively correspond to a first damping ring and a second damping ring of the plurality of damping rings such that the first and second isolation structures are respectively radially aligned with the first and second damping rings.

Example 3

The ultrasonic surgical instrument of Example 2, wherein each of the first and second isolation structures of the acoustic waveguide is formed as a cylindrical projection extending from the acoustic body of the acoustic waveguide.

Example 4

The ultrasonic surgical instrument of Examples 2 or 3, wherein each of the first and second isolation structures of the acoustic waveguide is formed as a flange extending from the acoustic body of the acoustic waveguide.

Example 5

The ultrasonic surgical instrument of any one or more of Examples 2 through 4, wherein the sheath body defines an inner diameter, and wherein each of the first and second radial diameters are substantially the same as the inner diameter.

Example 6

The ultrasonic surgical instrument of any one or more of Examples 1 through 5, wherein the sheath defines an elongate hollow cylindrical shape.

Example 7

The ultrasonic surgical instrument of any one or more of Examples 1 through 5, wherein the inner diameter of the sheath body is substantially the same along a longitudinal length of the sheath.

Example 8

The ultrasonic surgical instrument of any one or more of Examples 2 through 5, wherein the first radial diameter is substantially the same as the second radial diameter.

Example 9

The ultrasonic surgical instrument of any one or more of Examples 2 through 5, wherein the sheath is configured to engage the tube and at least one of the first or second isolation structures to provide a fluid seal between the tube and at least one of the first or second isolation structures for inhibiting fluid ingress along the shaft assembly.

Example 10

The ultrasonic surgical instrument of any one or more of Examples 1 through 9, wherein the ultrasonic blade includes a blade isolation structure radially extending therefrom, and wherein the sheath covers at least a portion of the blade isolation structure.

Example 11

The ultrasonic surgical instrument of any one or more of Examples 1 through 10, wherein each of the plurality of damping rings comprises an acoustically insulative material.

Example 12

The ultrasonic surgical instrument of Example 11, wherein each of the plurality of damping rings comprises a silicon material.

Example 13

The ultrasonic surgical instrument of any one or more of Examples 1 through 12, wherein each of the plurality of damping rings is bonded to the outer body surface of the sheath body.

Example 14

The ultrasonic surgical instrument of any one or more of Examples 1 through 13, wherein each of the plurality of damping rings comprises a material overmolded to the outer body surface of the sheath body.

Example 15

The ultrasonic surgical instrument of any one or more of Examples 1 through 14, wherein the shaft assembly further includes a sheath cap secured to a distal end of the sheath, wherein the sheath cap is configured to engage the acoustic waveguide and the tube to provide a fluid seal between the acoustic waveguide and the tube for inhibiting fluid ingress along the shaft assembly.

Example 16

An ultrasonic surgical instrument, comprising: an end effector including an ultrasonic blade; an ultrasonic transducer assembly; and a shaft assembly, including: a tube, an acoustic waveguide received within the tube and acoustically connected between the ultrasonic blade and ultrasonic transducer assembly to communicate ultrasonic vibrations from the ultrasonic transducer assembly to the ultrasonic blade, wherein the acoustic waveguide extends along a longitudinal axis, and a sheath radially positioned between the acoustic waveguide and the tube and including: a sheath body having a distal sheath end portion, and a sheath cap disposed on the distal sheath end portion of the sheath and positioned between the acoustic waveguide and tube, wherein the sheath cap is configured to acoustically isolate the acoustic waveguide from the tube or provide a fluid seal between the acoustic waveguide and the tube for inhibiting fluid ingress along the shaft assembly.

Example 17

The ultrasonic surgical instrument of Example 16, wherein the acoustic waveguide extends axially through the sheath cap, and wherein the sheath cap is configured to engage the acoustic waveguide and the tube such that the sheath cap is configured to provide the fluid seal between the acoustic waveguide and the tube.

Example 18

The ultrasonic surgical instrument of Examples 16 or 17, wherein the sheath further includes a plurality of damping rings extending radially outward from the sheath body toward the tube.

Example 19

The ultrasonic surgical instrument of Example 18, wherein the acoustic waveguide further includes: an acoustic body extending along the longitudinal axis and defining a body radial diameter about the longitudinal axis, a first isolation structure radially extending about the acoustic body a first radial diameter, wherein the first radial diameter is larger than the body radial diameter, and a second isolation structure radially extending about the acoustic body a second radial diameter and longitudinally spaced from the first isolation structure, wherein the first second radial diameters are larger than the body radial diameter, wherein the first and the second isolation structures respectively correspond to a first damping ring and a second damping ring of the plurality of damping rings such that the first and second isolation structures are respectively radially aligned with the first and second damping rings.

Example 20

A robotic surgical system, comprising: a patient support; a robotic arm moveable relative to the patient support; an ultrasonic surgical instrument, including: an end effector including an ultrasonic blade; an ultrasonic transducer assembly; and a shaft assembly, including: a tube, an acoustic waveguide received within the tube and acoustically connected between the ultrasonic blade and ultrasonic transducer assembly to communicate ultrasonic vibrations from the ultrasonic transducer assembly to the ultrasonic blade, wherein the acoustic waveguide extends along a longitudinal axis, and a sheath radially positioned between the acoustic waveguide and the tube and including: a sheath body having an outer body surface, and a plurality of damping rings radially extending from the outer body surface and engaged with the tube, wherein the plurality of damping rings are configured to acoustically isolate the acoustic waveguide from the tube.

Example 21

The robotic surgical system of Example 20, wherein the ultrasonic surgical instrument further comprises a carrier and a transducer associated with the ultrasonic transducer assembly, the carrier comprising a transducer housing configured to receive the transducer, the transducer comprising a grounding structure, wherein the grounding structure is configured to mechanically ground the transducer relative to the carrier.

Example 22

The robotic surgical system of Example 21, wherein the acoustic waveguide further comprises a ground bore and a ground pin received within the ground bore, wherein the ground pin is configured to engage a portion of the carrier to mechanically ground the acoustic waveguide relative to the portion of the carrier.

Example 23

The robotic surgical system of any one or more of Examples 20 through 22, wherein each damping ring is bonded to an exterior surface of the sheath.

Example 24

The robotic surgical system of any one or more of Examples 20 through 23, wherein each damping ring is positioned between the sheath and the tube.

Example 25

The robotic surgical system of any one or more of Examples 20 through 24, the shaft assembly further comprising a sheath cap positioned on a distal end of the sheath, wherein at least a portion of the sheath cap extends between the acoustic waveguide and the tube.

Example 26

The robotic surgical system of Example 25, wherein the sheath cap is configured to provide a fluid tight seal between the tube and the acoustic waveguide.

Example 27

The robotic surgical system of Examples 25 or 26, wherein the sheath cap is configured to acoustically isolate a portion of the acoustic waveguide from the tube.

VI. Miscellaneous

Any one or more of the teaching, expressions, embodiments, examples, etc. described herein may be combined with any one or more of the teachings, expressions, embodiments, examples, etc. described in U.S. patent application Ser. No. 17/077,067, entitled "Surgical Instrument and Carrier Kart Supporting Ultrasonic Transducer," filed on Oct. 22, 2020published as U.S. Pub. No. 2022/0125465 on Apr. 28, 2022; U.S. patent application Ser. No. 17/077,086, entitled "Carrier Kart and Jaw Closure of an Ultrasonic Surgical Instrument," filed on Oct. 22, 2020, published as U.S. Pub. No. 2022/0125466 on Apr. 28, 2022; U.S. patent application Ser. No. 17/077,130, entitled "Surgical Instrument with Clamping Sensor Feedback and Related Methods," filed on Oct. 22, 2020, published as U.S. Pub. No. 2022/0125470 on Apr. 28, 2022; U.S. patent application Ser.

No. 17/077,136, entitled "Surgical Instrument with Non-clamping Sensor Feedback and Related Methods," filed on Oct. 22, 2020, published as U.S. Pub. No. 2022/0125470 on Apr. 28, 2022; U.S. patent application Ser. No. 17/077,250, entitled "Ultrasonic Surgical Instrument with a Carrier Kart and Reusable Stage," filed on Oct. 22, 2020, published as U.S. Pub. No. 2022/0125472 on Apr. 28, 2022; U.S. patent application Ser. No. 17/077,373, entitled "Surgical Instrument with a Carrier Kart and Various Communication Cable Arrangements," filed on Oct. 22, 2020, published as U.S. Pub. No. 2022/0125473 on Apr. 28, 2022; U.S. patent application Ser. No. 17/077,139, entitled "Ultrasonic Surgical Instrument with a Fixed Transducer Grounding," filed on Oct. 22, 2020, published as U.S. Pub. No. 2022/0125471 on Apr. 28, 2022; U.S. patent application Ser. No. 17/077,146, entitled "Ultrasonic Surgical Instrument with a Shaft Assembly and Elongated Waveguide Support Arrangement," filed on Oct. 22, 2020, published as U.S. Pub. No. 2022/0125460 on Apr. 28, 2022; U.S. patent application Ser. No. 17/077,110, entitled "Ultrasonic Surgical Instrument with a Midshaft Closure System and Related Methods," filed on Oct. 22, 2020, published as U.S. Pub. No. 2022/0125468 on Apr. 28, 2022; U.S. patent application Ser. No. 17/076,956, entitled "Surgical Instrument with an Articulatable Shaft Assembly and Dual End Effector Roll," filed on Oct. 22, 2020, published as U.S. Pub. No. 2022/0125463 on Apr. 28, 2022; U.S. patent application Ser. No. 17/076,959, entitled "Ultrasonic Surgical Instrument with a Distally Grounded Acoustic Waveguide," filed on Oct. 22, 2020, published as U.S. Pub. No. 2022/0125464 on Apr. 28, 2022; and/or U.S. patent application Ser. No. 17/077,098, entitled "Ultrasonic Surgical Instrument with a Multiplanar Articulation Joint," filed on Oct. 22, 2020, published as U.S. Pub. No. 2022/0125467 on Apr. 28, 2022. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
    (a) an end effector including an ultrasonic blade;
    (b) an ultrasonic transducer assembly; and
    (c) a shaft assembly, including:
        (i) a tube,
        (ii) an acoustic waveguide received within the tube and acoustically connected between the ultrasonic blade and ultrasonic transducer assembly to communicate ultrasonic vibrations from the ultrasonic transducer assembly to the ultrasonic blade, wherein the acoustic waveguide extends along a longitudinal axis, and
        (iii) a sheath radially positioned between the acoustic waveguide and the tube and including:
            (A) a sheath body having an outer body surface, and
            (B) a plurality of damping rings radially extending from the outer body surface and engaged with the tube,
        wherein the plurality of damping rings are configured to acoustically isolate the acoustic waveguide from the tube.

2. The ultrasonic surgical instrument of claim 1, wherein the acoustic waveguide further includes:
    (A) an acoustic body extending along the longitudinal axis and defining a body radial diameter about the longitudinal axis,
    (B) a first isolation structure radially extending about the acoustic body a first radial diameter, wherein the first radial diameter is larger than the body radial diameter, and
    (C) a second isolation structure radially extending about the acoustic body a second radial diameter and longitudinally spaced from the first isolation structure, wherein the first second radial diameters are larger than the body radial diameter, wherein the first and the second isolation structures respectively correspond to a first damping ring and a second damping ring of the plurality of damping rings such that the first and second isolation structures are respectively radially aligned with the first and second damping rings.

3. The ultrasonic surgical instrument of claim 2, wherein each of the first and second isolation structures of the acoustic waveguide is formed as a cylindrical projection extending from the acoustic body of the acoustic waveguide.

4. The ultrasonic surgical instrument of claim 2, wherein each of the first and second isolation structures of the acoustic waveguide is formed as a flange extending from the acoustic body of the acoustic waveguide.

5. The ultrasonic surgical instrument of claim 2, wherein the sheath body defines an inner diameter, and wherein each of the first and second radial diameters are substantially the same as the inner diameter.

6. The ultrasonic surgical instrument of claim 5, wherein the sheath defines an elongate hollow cylindrical shape.

7. The ultrasonic surgical instrument of claim 5, wherein the inner diameter of the sheath body is substantially the same along a longitudinal length of the sheath.

8. The ultrasonic surgical instrument of claim 2, wherein the first radial diameter is substantially the same as the second radial diameter.

9. The ultrasonic surgical instrument of claim 2, wherein the sheath is configured to engage the tube and at least one of the first or second isolation structures to provide a fluid seal between the tube and at least one of the first or second isolation structures for inhibiting fluid ingress along the shaft assembly.

10. The ultrasonic surgical instrument of claim 1, wherein the ultrasonic blade includes a blade isolation structure radially extending therefrom, and wherein the sheath covers at least a portion of the blade isolation structure.

11. The ultrasonic surgical instrument of claim 1, wherein each of the plurality of damping rings comprises an acoustically insulative material.

12. The ultrasonic surgical instrument of claim 11, wherein each of the plurality of damping rings comprises a silicon material.

13. The ultrasonic surgical instrument of claim 1, wherein each of the plurality of damping rings is bonded to the outer body surface of the sheath body.

14. The ultrasonic surgical instrument of claim 1, wherein each of the plurality of damping rings comprises a material overmolded to the outer body surface of the sheath body.

15. The ultrasonic surgical instrument of claim 1, wherein the shaft assembly further includes a sheath cap secured to a distal end of the sheath, wherein the sheath cap is configured to engage the acoustic waveguide and the tube to provide a fluid seal between the acoustic waveguide and the tube for inhibiting fluid ingress along the shaft assembly.

* * * * *